United States Patent
Diebold et al.

(10) Patent No.: US 10,006,852 B2
(45) Date of Patent: Jun. 26, 2018

(54) FLOW CYTOMETER WITH OPTICAL EQUALIZATION

(71) Applicant: Becton, Dickinson and Company, Franklin Lakes, NJ (US)

(72) Inventors: Eric D. Diebold, Los Angeles, CA (US); Keegan Owsley, Los Angeles, CA (US); Matthew Bahr, Diamond Bar, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 0 days. days.

(21) Appl. No.: 15/698,506

(22) Filed: Sep. 7, 2017

(65) Prior Publication Data

US 2018/0073974 A1 Mar. 15, 2018

Related U.S. Application Data

(60) Provisional application No. 62/393,976, filed on Sep. 13, 2016.

(51) Int. Cl.
*G01N 21/00* (2006.01)
*G01N 15/14* (2006.01)
(Continued)

(52) U.S. Cl.
CPC ........... *G01N 15/1434* (2013.01); *G02F 1/33* (2013.01); *H01S 3/0071* (2013.01); *G02F 2203/18* (2013.01); *G02F 2203/24* (2013.01)

(58) Field of Classification Search
CPC ........... G01N 15/1429; G01N 15/1434; G01N 21/64; G01N 21/645; G01N 21/6428;
(Continued)

(56) References Cited

U.S. PATENT DOCUMENTS 4,883,656 A 11/1989 Konrad et al.
5,111,332 A 5/1992 Kuwabara et al.
(Continued)

FOREIGN PATENT DOCUMENTS

DE 102010044013 A1 5/2012
JP 11-6719 A 1/1999
(Continued)

OTHER PUBLICATIONS

Bertero et al. "Iterative image reconstruction: a point of view," Proceedings of the Interdisciplinary Workshop on Mathematical Methods in Biomedical Imaging and Intensity-Modulated Radiation Therapy (IMRT), Oct. 31, 2007, pp. 1-25. Retrieved from the Internet: URL:http://homes.di.unimi.it/borghesejTeachingjintelligentSystemsjDocumentsjSymbolic/07.Berteropaper.pdf.
(Continued)

*Primary Examiner* — Hoa Pham
(74) *Attorney, Agent, or Firm* — Bret E. Field; Bozicevic, Field & Francis LLP

(57) ABSTRACT

Aspects of the present disclosure include methods for producing an output laser beam having two or more angularly deflected laser beams (e.g., for irradiating a sample in a flow stream) with a predetermined intensity profile. Systems for practicing the subject methods having a laser, an acousto-optic device, a radiofrequency generator and a controller for adjusting the amplitude of the radiofrequency drive signals to produce an output laser beam of angularly deflected laser beams with a predetermined intensity profile are also described.

20 Claims, 19 Drawing Sheets

(51) Int. Cl.
*G02F 1/33* (2006.01)
*H01S 3/00* (2006.01)

(58) Field of Classification Search
CPC .. G01N 2015/1006; G02B 21/16; G02F 1/33; G02F 2203/24; G02F 2203/18; H01S 3/0071
USPC ....... 356/246, 432–440, 335–343; 250/459.1
See application file for complete search history.

(56) References Cited

U.S. PATENT DOCUMENTS

| | | | |
|---|---|---|---|
| 5,192,870 | A | 3/1993 | Batchelder et al. |
| 5,293,213 | A | 3/1994 | Klein et al. |
| 5,296,911 | A | 3/1994 | Weyrauch et al. |
| 5,485,530 | A | 1/1996 | Lakowicz et al. |
| 5,504,337 | A | 4/1996 | Lakowicz et al. |
| 6,016,196 | A | 1/2000 | Mermelstein |
| 6,057,814 | A | 5/2000 | Kalt |
| 6,236,454 | B1 | 5/2001 | Almogy |
| 6,252,669 | B1 | 6/2001 | Drabarek |
| 6,271,924 | B1 | 8/2001 | Ngoi et al. |
| 6,297,884 | B1 | 10/2001 | Drabarek |
| 6,396,069 | B1 | 5/2002 | MacPherson et al. |
| 6,592,822 | B1 | 7/2003 | Chandler |
| 6,867,899 | B2 | 3/2005 | Knebel |
| 7,400,457 | B1 | 7/2008 | Cayer |
| 7,630,063 | B2 | 12/2009 | Padmanabhan et al. |
| 7,724,426 | B2 | 5/2010 | Yamashita et al. |
| 7,889,348 | B2 | 2/2011 | Tearney et al. |
| 8,184,279 | B2 | 5/2012 | Feldkhun |
| 8,253,938 | B2 | 8/2012 | Vacca et al. |
| 9,201,011 | B2 | 12/2015 | Kalkbrenner et al. |
| 9,423,353 | B2 | 8/2016 | Diebold et al. |
| 9,784,661 | B2 * | 10/2017 | Jalali ............... G01N 15/1434 |
| 2003/0031352 | A1 | 2/2003 | Nelson et al. |
| 2003/0226977 | A1 | 12/2003 | Storz et al. |
| 2005/0081245 | A1 | 4/2005 | Arad et al. |
| 2005/0121603 | A1 | 6/2005 | Seyfried et al. |
| 2008/0129298 | A1 | 6/2008 | Vaughan et al. |
| 2008/0285606 | A1 | 11/2008 | Kippenberg et al. |
| 2009/0237289 | A1 | 9/2009 | Stoddard |
| 2009/0323061 | A1 | 12/2009 | Novotny et al. |
| 2010/0210952 | A1 | 8/2010 | Taira et al. |
| 2010/0301024 | A1 | 12/2010 | Unrath |
| 2011/0192991 | A1 | 8/2011 | Fukumoto et al. |
| 2011/0317910 | A1 | 12/2011 | Suzuki |
| 2012/0270306 | A1 | 10/2012 | Vacca et al. |
| 2012/0294319 | A1 | 11/2012 | Maleki et al. |
| 2012/0307244 | A1 | 12/2012 | Sharpe et al. |
| 2015/0177133 | A1 | 6/2015 | Choi et al. |
| 2016/0003741 | A1 | 1/2016 | Diebold et al. |
| 2017/0102314 | A1 | 4/2017 | Diebold et al. |
| 2017/0138857 | A1 * | 5/2017 | Diebold ............. G01N 21/6408 |
| 2017/0227444 | A1 | 8/2017 | Jalai et al. |
| 2017/0242232 | A1 * | 8/2017 | Leger .................... G02B 21/16 |
| 2017/0268981 | A1 | 9/2017 | Diebold et al. |
| 2017/0328826 | A1 * | 11/2017 | Diebold ............. G01N 15/1475 |
| 2017/0350803 | A1 * | 12/2017 | Jalali ...................... G01N 21/64 |

FOREIGN PATENT DOCUMENTS

| | | |
|---|---|---|
| JP | 2008-9395 A | 1/2008 |
| JP | 2009-20492 A | 1/2009 |
| JP | 2009-509684 A | 3/2009 |
| JP | 2011-158413 A | 8/2011 |
| JP | 2011-191496 A | 9/2011 |
| WO | WO 93/09423 A1 | 5/1993 |
| WO | WO 03/029882 A2 | 4/2003 |
| WO | WO 2007/041412 A1 | 4/2007 |
| WO | WO 2007/066126 A1 | 6/2007 |
| WO | WO 2009/087392 A1 | 7/2009 |
| WO | WO 2011/023593 A1 | 3/2011 |
| WO | WO 2012/127907 A1 | 9/2012 |
| WO | WO 2014/110290 A1 | 7/2014 |
| WO | WO 2014/152048 A2 | 9/2014 |
| WO | WO 2015/143041 A1 | 9/2015 |
| WO | WO 2016/054293 A1 | 4/2016 |
| WO | WO 2017066404 A1 | 4/2017 |
| WO | WO 2017161247 A1 | 9/2017 |

OTHER PUBLICATIONS

Diebold et al. "Digitally synthesized beat frequency multiplexing for sub-millisecond fluorescence microscopy," Nature Photonics, Oct. 2013, vol. 7, No. 10, pp. 806-810, published online Sep. 22, 2013.

Digman et al. "Fluorescence correlation spectroscopy and fluorescence cross-correlation spectroscopy," Wiley Interdisciplinary Reviews, Systems Biology and Medicine, vol. 1, No. 2, Apr. 29, 2009, pp. 273-282.

Dutta et al. "Quantitative Statistical Methods for Image Quality Assessment," Theranostics, vol. 3, No. 10, Oct. 4, 2013, pp. 741-756.

Eisenstein, M. "Fluorescence microscopy gets a frequency boost", Nature Methods, Dec. 2013, vol. 10, No. 12, p. 1149.

Fessler, J. A. "Penalized weighted least-squares image reconstruction for positron emission tomography," IEEE Trans. Medical Imaging, vol. 13, No. 2, Jun. 1994, pp. 290-300.

Hanley et al. "Fluorescence lifetime imaging in an optically sectioning programmable array microscope (PAM)", Cytometry, Part A, vol. 67A, No. 2, Jan. 1, 2005, pp. 112-118.

Hoffman, Robert A. "Pulse Width for Particle Sizing," Current Protocols in Cytometry, 50, Unit 1.23, pp. 1.23.1-1.23.17 (Oct. 2009).

Sisan et al. "Event Ordering in Live-Cell Imaging Determined from Temporal Cross-Correlation Asymmetry," Biophysical Journal, vol. 98, No. 11, Jun. 1, 2010, pp. 2432-2441.

Subramaniam et al. "Photophysics of Green and Red Fluorescent Proteins: Implications for Quantitative Microscopy", Methods in Enzymology, vol. 360, Jan. 1, 2003, pp. 178-201.

Thews et al. "Cross Talk Free Fluorescence Cross Correlation Spectroscopy in Live Cells," Biophysical Journal, vol. 89, No. 3, Sep. 30, 2005, pp. 2069-2076.

Varma et al. "Fast image reconstruction for fluorescence microscopy," AIP Advances, vol. 2, No. 3, Sep. 17, 2012, pp. 32174-32174.

Wu et al. "Frequency Division Multiplexed Multichannel High-Speed Fluorescence Confocal Microscope," Biophysical Journal, vol. 91, Sep. 2006, pp. 2290-2296.

* cited by examiner

FLOW CYTOMETER WITH OPTICAL EQUALIZATION

CROSS-REFERENCE TO RELATED APPLICATION

Pursuant to 35 U.S.C. § 119(e), this application claims priority to the filing date of U.S. Provisional Patent Application Ser. No. 62/393,976, filed Sep. 13, 2016; the disclosure of which application is incorporated herein by reference.

INTRODUCTION

The characterization of analytes in biological fluids has become an integral part of medical diagnoses and assessments of overall health and wellness of a patient. In particular, analyte detection in physiological fluids, e.g., blood or blood derived products, can be important where the results may play a prominent role in the treatment protocol of a patient in a variety of disease conditions.

Flow cytometry is a well-known technique that is used routinely for cell counting, cell sorting, biomarker detection, among others. A flow cytometer typically includes a sample reservoir for receiving a fluid sample, such as a blood sample, and a sheath reservoir containing a sheath fluid. The flow cytometer transports the particles (including cells) in the fluid sample as a cell stream to a flow cell, while also directing the sheath fluid to the flow cell. Within the flow cell, a liquid sheath is formed around the cell stream to impart a substantially uniform velocity on the cell stream. The flow cell hydrodynamically focuses the cells within the stream to pass through the center of a light source in a flow cell. In a flow cytometry system, particles (typically cells) flowing through a flow cell are illuminated with laser radiation and the radiation emanating from the particles (e.g., fluorescence and/or scattered radiation) in response to such illumination is detected and analyzed. Conventional flow cytometry systems, however, suffer from a number of shortcomings. For example, in conventional flow cytometry systems, the use of wider core streams at high sample flow rates results typically in a reduction in resolution, e.g., due to non-uniform optical response of the illuminated particles. In such conventional systems, in order to ameliorate this problem, a wider laser spot with a Gaussian profile is used to ensure quasi-uniform illumination of the particles. Notwithstanding, a lower resolution is typically achieved compared to using a slower sample flow rate (i.e., a narrower core stream).

SUMMARY

The present invention relates generally to methods and systems for flow cytometry, and more particularly, to such methods and systems for digitally generating intensity-varied excitation beams and/or encoding the excitation positions of particles within an excitation beam. Aspects of the present disclosure include methods for producing an output laser beam having two or more angularly deflected laser beams (e.g., for irradiating a sample in a flow stream) with a predetermined intensity profile. Methods according to certain embodiments include irradiating an acousto-optic device with a laser; applying radiofrequency drive signals to the acousto-optic device to generate angularly deflected laser beams and adjusting the amplitude of one or more of the radiofrequency drive signals to generate an output laser beam having angularly deflected laser beams with a predetermined intensity profile. Methods also include irradiating a sample in a flow stream with the output laser beam having the angularly deflected laser beams and detecting light from the sample in the flow stream. Systems for practicing the subject methods having a laser, an acousto-optic device, a radiofrequency generator and a controller for adjusting the amplitude of the radiofrequency drive signals to produce an output laser beam of angularly deflected laser beams with a predetermined intensity profile are also described. Kits having an acousto-optic device (e.g., acousto-optic deflector) and a flow cell configured to propagate a sample in flow stream are also provided.

In one aspect, a method for generating an excitation beam for use in a flow cytometry system is disclosed, which comprises introducing a laser beam into an acousto-optic device (e.g., an acousto-optic deflector), applying a plurality of radiofrequency signals to the acousto-optic device so as to generate a plurality of angularly deflected beams (which can be partially overlapping) collectively forming an output excitation beam, and adjusting amplitudes of the radiofrequency signals such that the output excitation beam exhibits a desired intensity profile, e.g., an intensity profile characterized by a desired intensity variation along one dimension, such as the horizontal dimension, of the beam.

For example, the excitation beam can exhibit an intensity variation along its horizontal dimension characterized by an intensity increase from the center of the beam to each horizontal edge thereof. In some such embodiments, the beam intensity at the center of the beam varies by a value in a range of about 0.1% to about 99% relative to the beam intensity at any of its horizontal edges. In some embodiments, such a variation can be linear while in others it can be nonlinear. In some embodiments, the beam's intensity profile along a vertical dimension can be Gaussian.

In some embodiments, the amplitudes of the radiofrequency signals are in a range of about 0.1 volts to about 40 volts. In some embodiments, the radiofrequency signals span a frequency range of about 1 MHz to about 250 MHz. Further, in some embodiments, the radiofrequency signals are separated from one another by a frequency in a range of about 0.1 MHz to about 4 MHz.

In some embodiments, the amplitudes of the radiofrequency signals are adjusted such that the deflected beams exhibit an increasing intensity as the deflection angles of the beams increase from a center beam.

In a related aspect, a flow cytometry system is disclosed, which comprises a flow cell through which a plurality of particles can flow, a laser for generating a laser beam, an acousto-optic deflector receiving the laser beam, and at least one radiofrequency generator for applying a plurality of radiofrequency signals to the acousto-optic deflector so as to generate a plurality of angularly deflected beams (which can be partially overlapping) collectively forming an output excitation beam for illuminating a plurality of particles flowing through the flow cell. A controller is coupled to the radiofrequency generator for adjusting amplitudes of said radiofrequency signals so as to impart a intensity profile to said excitation beam along at least one dimension (e.g., the horizontal dimension).

The system can further include a detection system for detecting radiation emanating from the illuminated particles in response to the illumination by the excitation beam. The intensity profile can be configured such that equivalent particles interacting with the beam at different locations thereof produce uniform signals. By way of example, in some embodiments, the beam intensity variation is characterized by an intensity increase from a center of the beam to each horizontal edge thereof. In some such embodiments, the beam intensity at the center of the beam varies by a value in a range of about 0.1% to about 99% (e.g., by at least about 50%) relative to the intensity of the beam at each of the horizontal edges. In some embodiments, the beam exhibits a Gaussian intensity profile in a vertical dimension.

The powers of the radiofrequency signals can be adjusted so as to obtain a desired variation of intensity (e.g., along the horizontal dimension) of the beam. In some embodiments, the controller can adjust the powers of the radiofrequency signals by adjusting the amplitudes of those signals in a range of about 0.1 volts to about 40 volts. Further, in some embodiments, the controller can control the radiofrequency generator so as to generate a plurality of radiofrequency signals that are separated from one another by a frequency in a range of about 0.1 MHz to about 4 MHz.

One or more excitation optics can be used to deliver the excitation beam into a flow cell through which a sample flows. By way of example, such excitation optics can include at least one lens for focusing the excitation beam into the flow cell. Further, the detection system can include at least one detector and one or more detection optics positioned at a 90-degree angle relative to the propagation direction of the excitation beam for transmitting the radiation emanating from illuminated particles, e.g., cells, passing through the flow cell to the detector.

In a related aspect, a method for adjusting an intensity profile of an excitation beam in a flow cytometry system is disclosed, which includes introducing a laser beam into an acousto-optic device (e.g., an acousto-optic deflector), applying a plurality of radiofrequency signals to the acousto-optic device to generate a plurality of angularly separated output beams, and adjusting powers of the radiofrequency signals to obtain desired intensities of said angularly separated output beams. The angularly-separated output beam can be arranged relative to one another so as to form collectively an excitation beam for illuminating a plurality of particles flowing through a flow cell of the flow cytometry system. In some embodiments, the powers of the radiofrequency signals are adjusted such that the excitation beam exhibits a higher intensity at each horizontal edge thereof relative to its center. By way of example, the variation of the intensity along a horizontal dimension of the beam can range from about 0.1% to about 99%.

In some embodiments, the amplitudes of the radiofrequency signals are varied in a range of about 0.1 volt to about 40 volts to adjust the powers of the radiofrequency signals. Further, in some embodiments, the radiofrequency signals are separated in frequency from one another by a value in a range of about 0.1 MHz to about 4 MHz.

In a related aspect, a flow cytometry system is disclosed, which includes a flow cell through which a plurality of particles can flow, a laser for generating a laser beam, an acousto-optic device receiving the laser beam, and at least one radiofrequency generator for applying a plurality of radiofrequency signals to the acousto-optic device so as to generate a plurality angularly-deflected beamlets separated in frequency by the radiofrequency signals and collectively forming a radiofrequency-shifted laser beam. The system can further include a beam splitter for splitting the radiofrequency-shifted laser beam into a pair of split radiofrequency-shifted laser beams such that each of the split beams includes a plurality of angularly-deflected beamlets separated in frequency by the radiofrequency signals, and at least one optic for horizontally inverting one of the pair of laser beams. The system also includes an optical combiner for combining the horizontally inverted beam with the other beam of the pair such that each of the beamlets in the horizontally inverted beam at least partially overlaps with at least one of the beamlets in the other beam of the pair so as to generate an excitation beam for illuminating the particles as they flow through the flow cell. The system can also include at least one detector for detecting forward scatter radiation emanating from one or more of the particles in response to excitation from the excitation beam and generating a detection signal. Further, the system can include a detection system arranged along 90-degree direction relative to the propagation direction of the excitation beam to detect radiation emanating from the particles in an orthogonal direction relative to the forward scatter direction.

The above system can also include an analyzer for receiving the detection signal and providing frequency de-multiplexing of the detection signal so as to determine one or more beat frequencies, wherein each of the beat frequencies corresponds to a frequency difference between a pair of beamlets (e.g., a pair of partially overlapping beamlets) in said excitation beam. The analyzer can correlate the beat frequencies with spatial locations across the excitation beam. Further, the analyzer can normalize the intensity of a detected signal (e.g., the forward scatter signal) based on the spatial location across the excitation beam that is associated with the beat frequency present in a frequency content of the signal.

The system can further include a controller coupled to the radiofrequency generator for adjusting the powers of the radiofrequency signals so as to adjust the intensities of the beamlets such that the intensity of the radiofrequency-shifted beam varies along a horizontal dimension. In some embodiments, the radiofrequency signals can be shifted in frequency relative to one another by a frequency in a range of about 10 MHz to about 250 MHz.

In another aspect, a method of adjusting spatial position of an excitation beam in a flow cytometer is disclosed, which includes introducing a laser beam into an acousto-optic deflector, applying a plurality of radiofrequency signals to said acousto-optic deflector so as to generate a plurality of angularly deflected beams (which can be partially overlapping) collectively forming an output excitation beam, introducing the excitation beam into a flow cell to interact with a sample stream flowing through the flow cell, monitoring a signal generated via detection of radiation emanating from the sample in response to interaction with the excitation beam to detect a spatial drift, if any, in the sample stream, and adjusting the radiofrequency signals so as to adjust a spatial position of the excitation beam in the flow cell so as to compensate for the detected drift in the sample stream. In some embodiments, the frequencies of the radiofrequency signals are adjusted so as to cause a shift in the spatial position of the excitation beam.

In another aspect, a method of adjusting a width of an excitation beam in a flow cytometer is disclosed, which includes introducing a laser beam into an acousto-optic deflector, applying a plurality of radiofrequency signals to said acousto-optic deflector so as to generate a plurality of angularly deflected beams (which can be partially overlapping) collectively forming an output excitation beam, and adjusting a number of said radiofrequency signals so as to adjust a width of said excitation beam.

BRIEF DESCRIPTION OF THE FIGURES

The invention may be best understood from the following detailed description when read in conjunction with the accompanying drawings. Included in the drawings are the following figures.

DETAILED DESCRIPTION

Figure 1:
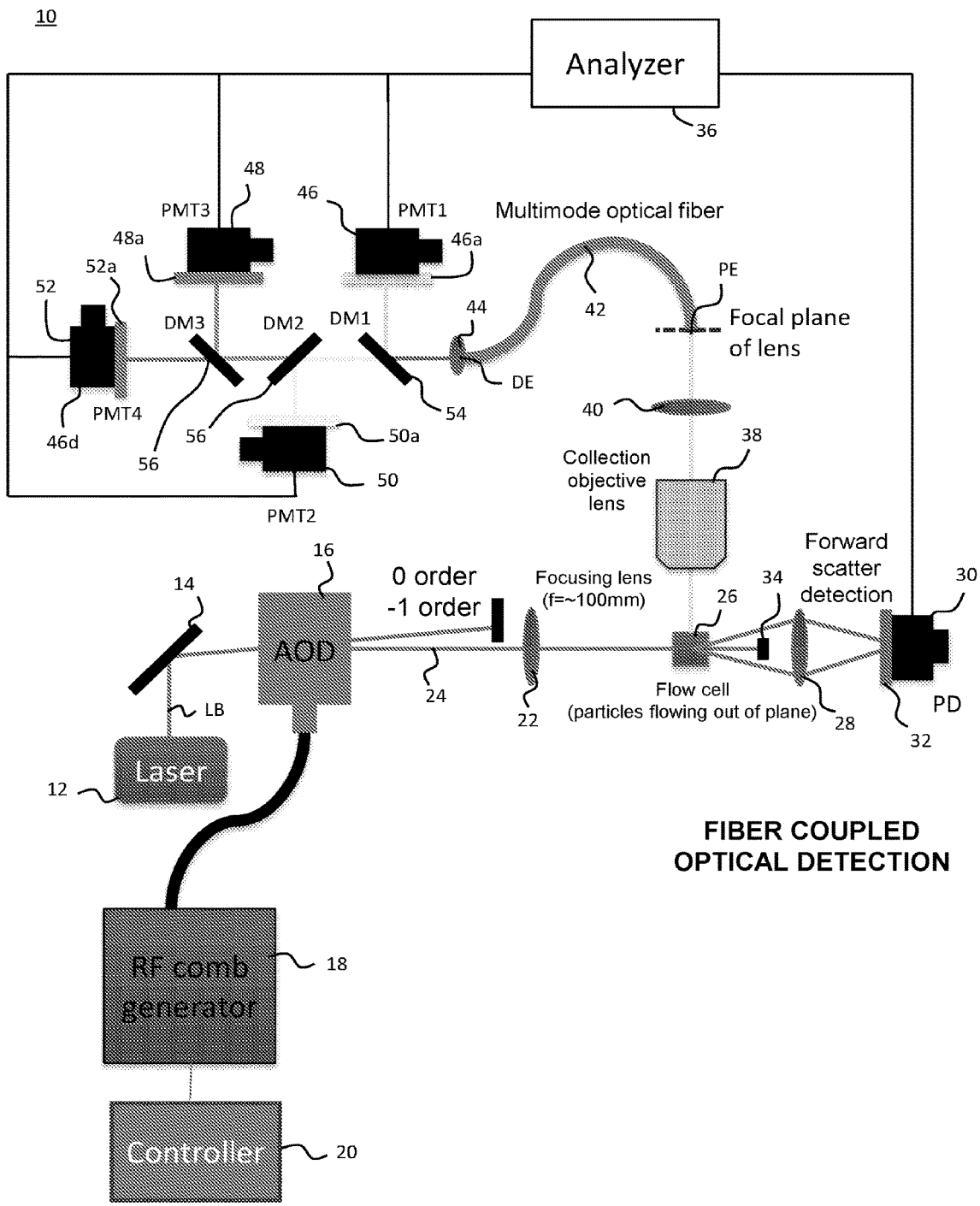
FIG. 1 schematically depicts a flow cytometry system according to an embodiment of the invention.

Aspects of the present disclosure include methods for producing an output laser beam having two or more angularly deflected laser beams (e.g., for irradiating a sample in a flow stream) with a predetermined intensity profile. Methods according to certain embodiments include irradiating an acousto-optic device with a laser; applying radiofrequency drive signals to the acousto-optic device to generate angularly deflected laser beams and adjusting the amplitude of one or more of the radiofrequency drive signals to generate an output laser beam having angularly deflected laser beams with a predetermined intensity profile. Methods also include irradiating a sample in a flow stream with the output laser beam having the angularly deflected laser beams and detecting light from the sample in the flow stream. Systems for practicing the subject methods having a laser, an acousto-optic device, a radiofrequency generator and a controller for adjusting the amplitude of the radiofrequency drive signals to produce an output laser beam of angularly deflected laser beams with a predetermined intensity profile are also described. Kits having an acousto-optic device (e.g., acousto-optic deflector) and a flow cell configured to propagate a sample in flow stream are also provided.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the present disclosure provides methods for producing an output laser beam having two or more angularly deflected laser beams (e.g., for irradiating a sample in a flow stream) with a predetermined intensity profile. In further describing embodiments of the disclosure, methods for producing an output laser beam having two or more angularly deflected laser beams and adjusting the amplitude of each angularly deflected laser beam are first described in greater detail. Next, systems for practicing the subject methods having a laser, an acousto-optic device, a radiofrequency generator and a controller for adjusting the amplitude of the radiofrequency drive signals to produce an output laser beam of angularly deflected laser beams with a predetermined intensity profile are also described. Kits having an acousto-optic device and a flow cell configured to propagate a sample in flow stream are also provided.

Methods for Producing an Output Laser Beam Having Angularly Deflected Laser Beams with a Predetermined Intensity Profile Aspects of the disclosure include methods for producing an output laser beam having two or more angularly deflected laser beams (e.g., for irradiating a sample in a flow stream) with a predetermined intensity profile. In practicing methods according to embodiments, an acousto-optic device is irradiated with a laser while applying radiofrequency drive signals to the acousto-optic device to generate angularly deflected laser beams and adjusting the amplitude of one or more of the radiofrequency drive signals to generate an output laser beam that comprises angularly deflected laser beams with a predetermined intensity profile. Each angularly deflected laser beam in the output laser beam has an intensity that is based on the amplitude of each applied radiofrequency drive signal. The term "angularly deflected laser beam" is used herein in its conventional sense to refer to laser beams that are produced via the interaction of acoustic waves in the acousto-optic device, produced by the applied radiofrequency drive signals, with the beam of light from the laser to produce one or more beamlets having a shift in optical frequency and a deflection in propagation angle.

In embodiments, methods include irradiating the acousto-optic device with a laser. Lasers of interest may include pulsed lasers or continuous wave lasers. The type and number of lasers used in the subject methods may vary and may be a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof. In others instances, the methods include irradiating the acousto-optic device with a dye laser, such as a stilbene, coumarin or rhodamine laser. In yet other instances, methods include irradiating the acousto-optic device with a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof. In still other instances, methods include irradiating the acousto-optic device with a solid-state laser, such as a ruby laser, an Nd:YAG laser, NdCrYAG laser, Er:YAG laser, Nd:YLF laser, Nd:YVO$_4$ laser, Nd:YCa$_4$O($BO_3$)$_3$ laser, Nd:YCOB laser, titanium sapphire laser, thulium YAG laser, ytterbium YAG laser, ytterbium$_2$O$_3$ laser or cerium doped lasers and combinations thereof. In still other instances, methods include irradiating the acousto-optic device with a semiconductor diode laser, optically pumped semiconductor laser (OPSL), or a frequency doubled- or frequency tripled implementation of any of the above mentioned lasers.

Depending on the desired wavelengths of light produced in the output laser beam (e.g., for use in irradiating a sample in a flow stream), the laser may have a specific wavelength that varies from 200 nm to 1500 nm, such as from 250 nm to 1250 nm, such as from 300 nm to 1000 nm, such as from 350 nm to 900 nm and including from 400 nm to 800 nm. The acousto-optic device may be irradiated with one or more lasers, such as 2 or more lasers, such as 3 or more lasers, such as 4 or more lasers, such as 5 or more lasers and including 10 or more lasers. The lasers may include any combination of types of lasers. For example, in some embodiments, the methods include irradiating the acousto-optic device with an array of lasers, such as an array having one or more gas lasers, one or more dye lasers and one or more solid-state lasers.

Where more than laser is employed, the acousto-optic device may be irradiated with the lasers simultaneously or sequentially, or a combination thereof. For example, the acousto-optic device may be simultaneously irradiated with each of the lasers. In other embodiments, the acousto-optic device is sequentially irradiated with each of the lasers. Where more than one laser is employed to irradiate the acousto-optic device sequentially, the time each laser irradiates the acousto-optic device may independently be 0.001 microseconds or more, such as 0.01 microseconds or more, such as 0.1 microseconds or more, such as 1 microsecond or more, such as 5 microseconds or more, such as 10 microseconds or more, such as 30 microseconds or more and including 60 microseconds or more. For example, methods may include irradiating the acousto-optic device with the laser for a duration which ranges from 0.001 microseconds to 100 microseconds, such as from 0.01 microseconds to 75 microseconds, such as from 0.1 microseconds to 50 microseconds, such as from 1 microsecond to 25 microseconds and including from 5 microseconds to 10 microseconds. In embodiments where acousto-optic device is sequentially irradiated with two or more lasers, the duration the acousto-optic device is irradiated by each laser may be the same or different.

The time period between irradiation by each laser may also vary, as desired, being separated independently by a delay of 0.001 microseconds or more, such as 0.01 microseconds or more, such as 0.1 microseconds or more, such as 1 microsecond or more, such as 5 microseconds or more, such as by 10 microseconds or more, such as by 15 microseconds or more, such as by 30 microseconds or more and including by 60 microseconds or more. For example, the time period between irradiation by each light source may range from 0.001 microseconds to 60 microseconds, such as from 0.01 microseconds to 50 microseconds, such as from 0.1 microseconds to 35 microseconds, such as from 1 microsecond to 25 microseconds and including from 5 microseconds to 10 microseconds. In certain embodiments, the time period between irradiation by each laser is 10 microseconds. In embodiments where the acousto-optic device is sequentially irradiated by more than two (i.e., 3 or more) lasers, the delay between irradiation by each laser may be the same or different.

The acousto-optic device may be irradiated continuously or in discrete intervals. In some instances, methods include irradiating the acousto-optic device with the laser continuously. In other instances, the acousto-optic device is irradiated with the laser in discrete intervals, such as irradiating every 0.001 millisecond, every 0.01 millisecond, every 0.1 millisecond, every 1 millisecond, every 10 milliseconds, every 100 milliseconds and including every 1000 milliseconds, or some other interval.

Depending on the laser, the acousto-optic device may be irradiated from a distance which varies such as 0.01 mm or more, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more. Also, the angle or irradiation may also vary, ranging from 10° to 90°, such as from 15° to 85°, such as from 20° to 80°, such as from 25° to 75° and including from 30° to 60°, for example at a 90° angle.

In embodiments, methods include applying radiofrequency drive signals to the acousto-optic device to generate angularly deflected laser beams and adjusting the amplitude of one or more of the radiofrequency drive signals to generate an output laser beam that comprises angularly deflected laser beams with a predetermined intensity profile. Two or more radiofrequency drive signals may be applied to the acousto-optic device to generate an output laser beam with the desired number of angularly deflected laser beams, such as 3 or more radiofrequency drive signals, such as 4 or more radiofrequency drive signals, such as 5 or more radiofrequency drive signals, such as 6 or more radiofrequency drive signals, such as 7 or more radiofrequency drive signals, such as 8 or more radiofrequency drive signals, such as 9 or more radiofrequency drive signals, such as 10 or more radiofrequency drive signals, such as 15 or more radiofrequency drive signals, such as 25 or more radiofrequency drive signals, such as 50 or more radiofrequency drive signals and including 100 or more radiofrequency drive signals.

The angularly deflected laser beams produced by the radiofrequency drive signals each have an intensity based on the amplitude of the applied radiofrequency drive signal. In embodiments, methods include applying radiofrequency drive signals having amplitudes sufficient to produce angularly deflected laser beams with a desired intensity. In some embodiments, each applied radiofrequency drive signal independently has an amplitude from about 0.001 V to about 500 V, such as from about 0.005 V to about 400 V, such as from about 0.01 V to about 300 V, such as from about 0.05 V to about 200 V, such as from about 0.1 V to about 100 V, such as from about 0.5 V to about 75 V, such as from about 1 V to 50 V, such as from about 2 V to 40 V, such as from 3 V to about 30 V and including from about 5 V to about 25 V. Each applied radiofrequency drive signal has, in some embodiments, a frequency of from about 0.001 MHz to about 500 MHz, such as from about 0.005 MHz to about 400 MHz, such as from about 0.01 MHz to about 300 MHz, such as from about 0.05 MHz to about 200 MHz, such as from about 0.1 MHz to about 100 MHz, such as from about 0.5 MHz to about 90 MHz, such as from about 1 MHz to about 75 MHz, such as from about 2 MHz to about 70 MHz, such as from about 3 MHz to about 65 MHz, such as from about 4 MHz to about 60 MHz and including from about 5 MHz to about 50 MHz.

As summarized above, the output laser beam from the acousto-optic device includes angularly deflected laser beams each having an intensity based on the amplitude of the applied radiofrequency drive signal. In some embodiments, methods include applying radiofrequency drive signals to the acousto-optic device in a manner sufficient to produce an output laser beam with angularly deflected laser beams having a desired intensity profile. Depending on the number of angularly deflected laser beams in the output laser, two or more of the angularly deflected laser beams may be adjusted to have the same intensity, such as where 3 or more angularly deflected laser beams have the same intensity, such as where 4 or more angularly deflected laser beams have the same intensity, such as where 5 or more angularly deflected laser beams have the same intensity, such as where 6 or more angularly deflected laser beams have the same intensity, such as where 7 or more angularly deflected laser beams have the same intensity, such as where 8 or more angularly deflected laser beams have the same intensity, such as where 9 or more angularly deflected laser beams have the same intensity, such as where 10 or more angularly deflected laser beams have the same intensity and including where 25 or more angularly deflected laser beams have the same intensity. In other embodiments, the number of angularly deflected laser beams in the output laser that have different intensities may vary, such as where 2 or more angularly deflected laser beams have different intensities, such as where 3 or more angularly deflected laser beams have different intensities, such as where 4 or more angularly deflected laser beams have different intensities, such as where 5 or more angularly deflected laser beams have different intensities, such as where 6 or more angularly deflected laser beams have different intensities, such as where 7 or more angularly deflected laser beams have different intensities, such as where 8 or more angularly deflected laser beams have different intensities, such as where 9 or more angularly deflected laser beams have different intensities, such as where 10 or more angularly deflected laser beams have different intensities and including where 25 or more angularly deflected laser beams have different intensities.

In some instances, the intensity profile of the angularly deflected laser beams in the output laser beam includes increasing intensity from the edges to the center of the output laser beam along the horizontal axis. In these instances, the intensity of the angularly deflected laser beam at the center of the output beam may range from 0.1% to about 99% of the intensity of the angularly deflected laser beams at the edge of the output laser beam along the horizontal axis, such as from 0.5% to about 95%, such as from 1% to about 90%, such as from about 2% to about 85%, such as from about 3% to about 80%, such as from about 4% to about 75%, such as from about 5% to about 70%, such as from about 6% to about 65%, such as from about 7% to about 60%, such as from about 8% to about 55% and including from about 10% to about 50% of the intensity of the angularly deflected laser beams at the edge of the output laser beam along the horizontal axis. In other instances, the intensity profile of the angularly deflected laser beams in the output laser beam includes an increasing intensity from the edges to the center of the output laser beam along the horizontal axis. In these instances, the intensity of the angularly deflected laser beam at the edges of the output beam may range from 0.1% to about 99% of the intensity of the angularly deflected laser beams at the center of the output laser beam along the horizontal axis, such as from 0.5% to about 95%, such as from 1% to about 90%, such as from about 2% to about 85%, such as from about 3% to about 80%, such as from about 4% to about 75%, such as from about 5% to about 70%, such as from about 6% to about 65%, such as from about 7% to about 60%, such as from about 8% to about 55% and including from about 10% to about 50% of the intensity of the angularly deflected laser beams at the center of the output laser beam along the horizontal axis. In still other instances, the intensity profile of the angularly deflected laser beams in the output laser beam includes a Gaussian distribution along the horizontal axis of the output laser beam. In yet other instances, the intensity profile of the angularly deflected laser beams in the output laser beam includes a top hat intensity profile along the horizontal axis.

In embodiments, the angularly deflected laser beams in the output laser beam are spatially separated. Depending on the applied radiofrequency drive signals and desired irradiation profile of the output laser beam, the angularly deflected laser beams may be separated by 0.001 µm or more, such as by 0.005 µm or more, such as by 0.01 µm or more, such as by 0.05 µm or more, such as by 0.1 µm or more, such as by 0.5 µm or more, such as by 1 µm or more, such as by 5 µm or more, such as by 10 µm or more, such as by 100 µm or more, such as by 500 µm or more, such as by 1000 µm or more and including by 5000 µm or more. In some embodiments, the angularly deflected laser beams overlap, such as with an adjacent angularly deflected laser beam along a horizontal axis of the output laser beam. The overlap between adjacent angularly deflected laser beams (such as overlap of beam spots) may be an overlap of 0.001 µm or more, such as an overlap of 0.005 µm or more, such as an overlap of 0.01 µm or more, such as an overlap of 0.05 µm or more, such as an overlap of 0.1 µm or more, such as an overlap of 0.5 µm or more, such as an overlap of 1 µm or more, such as an overlap of 5 µm or more, such as an overlap of 10 µm or more and including an overlap of 100 µm or more.

In certain embodiments, methods include adjusting the spatial width of the output laser beam, such as adjusting the spatial width of the output laser beam along a horizontal axis of the output laser beam. Depending on the size of the output laser beam desired, the spatial width of the output laser beam may be increased by 0.001 µm or more, such as by 0.005 µm or more, such as by 0.01 µm or more, such as by 0.05 µm or more, such as by 0.1 µm or more, such as by 0.5 µm or more, such as by 1 µm or more, such as by 5 µm or more, such as by 10 µm or more, such as by 100 µm or more, such as by 500 µm or more, such as by 1000 µm or more and including by 5000 µm or more. In other embodiments, methods include decreasing the spatial width of the output laser beam by 0.001 µm or more, such as by 0.005 µm or more, such as by 0.01 µm or more, such as by 0.05 µm or more, such as by 0.1 µm or more, such as by 0.5 µm or more, such as by 1 µm or more, such as by 5 µm or more, such as by 10 µm or more, such as by 100 µm or more, such as by 500 µm or more, such as by 1000 µm or more and including by 5000 µm or more.

To adjust the spatial width of the output laser beam, methods include in certain embodiments increasing or decreasing the number of radiofrequency drive signals applied to the acousto-optic device during irradiation with the laser. In some embodiments, the spatial width of the output laser beam is decreased by reducing the number of angularly deflected laser beams in the output laser beam, such as by reducing the number of angularly deflected laser beams by 1 or more, such as by 2 or more, such as by 3 or more, such as by 5 or more, such as by 10 or more, such as by 25 or more and including by 100 or more. In these embodiments, methods include reducing the number of applied radiofrequency drive signals by 1 or more, such as by 2 or more, such as by 3 or more, such as by 5 or more, such as by 10 or more, such as by 25 or more and including by 100 or more. In other embodiments, the spatial width of the output laser beam is increased by increasing the number of angularly deflected laser beams in the output laser beam, such as by increasing the number of angularly deflected laser beams by 1 or more, such as by 2 or more, such as by 3 or more, such as by 5 or more, such as by 10 or more, such as by 25 or more and including by 100 or more. In these embodiments, methods include increasing the number of applied radiofrequency drive signals by 1 or more, such as by 2 or more, such as by 3 or more, such as by 5 or more, such as by 10 or more, such as by 25 or more and including by 100 or more.

In certain embodiments, methods include splitting the output laser beam into a first split laser beam having a first set of angularly deflected laser beams and a second split laser beam having a second set of angularly deflected laser beams from the output laser beam. In some embodiments the first split laser beam and the second split laser beam are identical and include the same number of angularly deflected laser beams with the same intensity profile. Any convenient optical adjustment protocol can be used to split the output laser beam, such as a dichroic mirror or a beam splitter. In these embodiments, methods may further include inverting one of the split laser beams (i.e., the first split laser beam or the second split laser beam) and optically combining the laser beams to produce a combined output laser beam where the angularly deflected laser beams of the inverted split laser beam overlaps with the angularly deflected laser beams of the non-inverted split laser beam. Any convenient optical adjustment protocol may be used to invert the split laser beam, including but not limited to lens, mirrors, prisms (e.g., dove prism), among other optical inversion protocols. As described in great detail below, when the inverted split laser beam is combined with the non-inverted split laser beam, each overlapping angularly deflected laser beam produces a beat frequency, which is the difference between the frequencies of the overlapping angularly deflected laser beams.

In some embodiments, methods include irradiating a sample in a flow stream (e.g., in a flow cytometer) with the output laser beam (or the combined output laser beam described above). In some embodiments, the sample is a biological sample. The term "biological sample" is used in its conventional sense to refer to a whole organism, plant, fungi or a subset of animal tissues, cells or component parts which may in certain instances be found in blood, mucus, lymphatic fluid, synovial fluid, cerebrospinal fluid, saliva, bronchoalveolar lavage, amniotic fluid, amniotic cord blood, urine, vaginal fluid and semen. As such, a "biological sample" refers to both the native organism or a subset of its tissues as well as to a homogenate, lysate or extract prepared from the organism or a subset of its tissues, including but not limited to, for example, plasma, serum, spinal fluid, lymph fluid, sections of the skin, respiratory, gastrointestinal, cardiovascular, and genitourinary tracts, tears, saliva, milk, blood cells, tumors, organs. Biological samples may be any type of organismic tissue, including both healthy and diseased tissue (e.g., cancerous, malignant, necrotic, etc.). In certain embodiments, the biological sample is a liquid sample, such as blood or derivative thereof, e.g., plasma, or other biological liquid sample, e.g., tears, urine, semen, etc., where in some instances the sample is a blood sample, including whole blood, such as blood obtained from venipuncture or fingerstick (where the blood may or may not be combined with any reagents prior to assay, such as preservatives, anticoagulants, etc.).

In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

In certain embodiments, the biological sample contains cells. Cells that may be present in the sample include eukaryotic cells (e.g., mammalian cells) and/or prokaryotic cells (e.g., bacterial cells or archaeal cells). Samples may be obtained from an in vitro source (e.g., a suspension of cells from laboratory cells grown in culture) or from an in vivo source (e.g., a mammalian subject, a human subject, etc.). In some embodiments, the cellular sample is obtained from an in vitro source. In vitro sources include, but are not limited to, prokaryotic (e.g., bacterial, archaeal) cell cultures, environmental samples that contain prokaryotic and/or eukaryotic (e.g., mammalian, protest, fungal, etc.) cells, eukaryotic cell cultures (e.g., cultures of established cell lines, cultures of known or purchased cell lines, cultures of immortalized cell lines, cultures of primary cells, cultures of laboratory yeast, etc.), tissue cultures, and the like.

Where the biological sample includes cells, methods of the present disclosure may include characterizing components of the cells, such as cell fragments, fragmented cell membranes, organelles, dead or lysed cells. In some embodiments, methods include characterizing the extracellular vesicles of the cells. Characterizing the extracellular vesicles of the cells may include identifying the type of extracellular vesicles in the cells or determining the size of the extracellular vesicles in the cells.

The sample in the flow stream may be irradiated continuously or in discrete intervals. In some instances, methods include irradiating the sample in the flow stream with the light source continuously. In other instances, the sample in the flow stream is irradiated with the light source in discrete intervals, such as irradiating every 0.001 millisecond, every 0.01 millisecond, every 0.1 millisecond, every 1 millisecond, every 10 milliseconds, every 100 milliseconds and including every 1000 milliseconds, or some other interval.

Depending on the light source, the sample in the flow stream may be irradiated from a distance which varies such as 0.01 mm or more, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more. Also, the angle or irradiation may also vary, ranging from 10° to 90°, such as from 15° to 85°, such as from 20° to 80°, such as from 25° to 75° and including from 30° to 60°, for example at a 90° angle.

The flow rate of the flow stream may vary, e.g., depending on the intensity of the light and may be 1 uL/min or more, such as 2 uL/min or more, such as 3 uL/min or more, such as 5 uL/min or more, such as 10 uL/min or more, such as 25 uL/min or more, such as 50 uL/min or more, such as 75 uL/min or more, such as 100 uL/min or more, such as 250 uL/min or more, such as 500 uL/min or more, such as 750 uL/min or more and including 1000 uL/min or more. In certain embodiments, the flow rate of the flow stream in the subject methods ranges from 1 uL/min to 500 uL/min, such as from 1 uL/min to 250 uL/min, such as from 1 uL/min to 100 uL/min, such as from 2 uL/min to 90 uL/min, such as from 3 uL/min to 80 uL/min, such as from 4 uL/min to 70 uL/min, such as from 5 uL/min to 60 uL/min and including from 10 uL/min to 50 uL/min. In certain embodiments, the flow rate of the flow stream is from 5 uL/min to 6 uL/min.

Methods also include detecting light from the sample in the flow stream. The light detected may be side scattered light, forward scattered light, emitted light or combination thereof. Suitable light detecting protocols, include but are not limited to optical sensors or photodetectors, such as active-pixel sensors (APSs), avalanche photodiode, image sensors, charge-coupled devices (CODs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, light from the irradiated flow stream at the sample interrogation region of the particle sorting module is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors. In certain embodiments, light is measured with a charge-coupled device (CCD).

In some embodiments, light (e.g., forward scattered light, side scattered light, emitted light, etc.) is detected directly from the sample in the flow stream. In other embodiments, light from the sample in the flow stream is propagated to a detector with one or more optical adjustment components. By "optical adjustment" is meant that light from the sample in the flow stream is changed as desired. For example, the beam path, direction, focus or collimation of the light from the sample in the flow stream may be changed with an optical adjustment component. In some instances, the dimensions of the light collected from the sample in the flow stream is adjusted, such as increasing the dimensions by 5% or more, such as by 10% or more, such as by 25% or more, such as by 50% or more and including increasing the dimensions by 75% or more or focusing the light so as to reduce the light dimensions, such as by 5% or greater, such as by 10% or greater, such as by 25% or greater, such as by 50% or greater and including reducing the dimensions by 75% or greater. In other instances, optical adjustment includes collimating the light. The term "collimate" is used in its conventional sense to refer to the optically adjusting the collinearity of light propagation or reducing divergence by the light of from a common axis of propagation. In some instances, collimating includes narrowing the spatial cross section of a light beam. In certain embodiments, the optical adjustment component is a wavelength separator. The term "wavelength separator" is used herein in its conventional sense to refer to an optical protocol for separating polychromatic light into its component wavelengths. Wavelength separation, according to certain embodiments, may include selectively passing or blocking specific wavelengths or wavelength ranges of the polychromatic light. Wavelength separation protocols of interest include, but are not limited to, colored glass, bandpass filters, interference filters, dichroic mirrors, diffraction gratings, monochromators and combinations thereof, among other wavelength separating protocols. In some embodiments, the wavelength separator is an optical filter. For example, the optical filter may be a bandpass filter having minimum bandwidths ranging from 2 nm to 100 nm, such as from 3 nm to 95 nm, such as from 5 nm to 95 nm, such as from 10 nm to 90 nm, such as from 12 nm to 85 nm, such as from 15 nm to 80 nm and including bandpass filters having minimum bandwidths ranging from 20 nm to 50 nm.

In certain embodiments, the detector is positioned apart in space from the sample in the flow stream and light from the sample in the flow stream is propagated to the detector through an optical relay system, such as with fiber optics or a free space light relay system. For example, the optical relay system may be a fiber optics light relay bundle and light is conveyed through the fiber optics light relay bundle to the detector. Any fiber optics light relay system may be employed to propagate light to the detector. In certain embodiments, suitable fiber optics light relay systems for propagating light to the detector include, but are not limited to, fiber optics light relay systems such as those described in U.S. Pat. No. 6,809,804, the disclosure of which is herein incorporated by reference. In other embodiments, the optical relay system is a free-space light relay system. The phrase "free-space light relay" is used herein in its conventional sense to refer to light propagation that employs a configuration of one or more optical components to direct light to the detector through free-space. In certain embodiments, the free-space light relay system includes a housing having a proximal end and a distal end, the proximal end being coupled to the detector. The free-space relay system may include any combination of different optical adjustment components, such as one or more of lenses, mirrors, slits, pinholes, wavelength separators, or a combination thereof. For example, in some embodiments, free-space light relay systems of interest include one or more focusing lens. In other embodiments, the subject free-space light relay systems include one or more mirrors. In yet other embodiments, the free-space light relay system includes a collimating lens. In certain embodiments, suitable free-space light relay systems for propagating light to the detector, but are not limited to, light relay systems such as those described in U.S. Pat. Nos. 7,643,142; 7,728,974 and 8,223,445, the disclosures of which is herein incorporated by reference.

Methods according to certain embodiments also include measuring light from the sample in the flow stream at one or more wavelengths, such as at 2 or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring light emitted by a sample in the flow stream at 400 or more different wavelengths. In some embodiments, methods include measuring the collected light over a range of wavelengths (e.g., 200 nm-1000 nm). For example, methods may include collecting spectra of light over one or more of the wavelength ranges of 200 nm-1000 nm. In yet other embodiments, methods include measuring collected light at one or more specific wavelengths. For example, the collected light may be measured at one or more of 450 nm, 518 nm, 519 nm, 561 nm, 578 nm, 605 nm, 607 nm, 625 nm, 650 nm, 660 nm, 667 nm, 670 nm, 668 nm, 695 nm, 710 nm, 723 nm, 780 nm, 785 nm, 647 nm, 617 nm and any combinations thereof. In certain embodiments, methods including measuring wavelengths of light which correspond to the fluorescence peak wavelength of certain fluorophores.

The collected light may be measured continuously or in discrete intervals. In some instances, methods include taking measurements of the light continuously. In other instances, the light is measured in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval.

Measurements of the collected light may be taken one or more times during the subject methods, such as 2 or more times, such as 3 or more times, such as 5 or more times and including 10 or more times. In certain embodiments, the light propagation is measured 2 or more times, with the data in certain instances being averaged.

Methods in certain embodiments also include data acquisition, analysis and recording, such as with a computer, where multiple data channels record data from the sample as it passes through the detection region of the system. In these embodiments, analysis may include classifying and counting cells or components of cells (extracellular vesicles) such that each component is present as a set of digitized parameter values. The subject systems may be set to trigger on a selected parameter in order to distinguish the particles of interest from background and noise. "Trigger" refers to a preset threshold for detection of a parameter and may be used as a means for detecting passage of a component of interest through the detection region. Detection of an event that exceeds the threshold for the selected parameter triggers acquisition of data for the sample component. Data is not acquired for components in the medium being assayed which cause a response below the threshold.

Systems for Producing an Output Laser Beam Having Angularly Deflected Laser Beams with a Predetermined Intensity Profile As summarized above, aspects of the present disclosure include systems configured for producing an output laser beam having two or more angularly deflected laser beams (e.g., for irradiating a sample in a flow stream) with a predetermined intensity profile. In embodiments, systems include a flow cell configured to propagate a sample in a flow stream, a laser, a radiofrequency generator configured to apply radiofrequency drive signals to the acousto-optic device to generate angularly deflected laser beams and a controller with a processor having memory operably coupled to the processor such that the memory has instructions stored thereon which when executed by the processor cause the processor to adjust the amplitudes of one or more of the radiofrequency drive signals to generate an output laser beam with angularly deflected laser beams having a desired intensity profile.

In embodiments, the subject systems include one or more lasers. Lasers of interest may include pulsed lasers or continuous wave lasers. The type and number of lasers used in the subject methods may vary and may be a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof. In others instances, the methods include irradiating the acousto-optic device with a dye laser, such as a stilbene, coumarin or rhodamine laser. In yet other instances, methods include irradiating the acousto-optic device with a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof. In still other instances, methods include irradiating the acousto-optic device with a solid-state laser, such as a ruby laser, an Nd:YAG laser, NdCrYAG laser, Er:YAG laser, Nd:YLF laser, Nd:YVO$_4$ laser, Nd:YCa$_4$O(BO$_3$)$_3$ laser, Nd:YCOB laser, titanium sapphire laser, thulim YAG laser, ytterbium YAG laser, ytterbium$_2$O$_3$ laser or cerium doped lasers and combinations thereof. In still other instances, methods include irradiating the acousto-optic device with a semiconductor diode laser, optically pumped semiconductor laser (OPSL), or a frequency doubled- or frequency tripled implementation of any of the above mentioned lasers.

The acousto-optic device may be any convenient acousto-optic protocol configured to frequency shift laser light using applied acoustic waves. In certain embodiments, the acousto-optic device is an acousto-optic deflector. The acousto-optic device in the subject system is configured to generate angularly deflected laser beams from the light from the laser and the applied radiofrequency drive signals. The radiofrequency drive signals may be applied to the acousto-optic device with any suitable radiofrequency drive signal source, such as a direct digital synthesizer (DDS), arbitrary waveform generator (AWG), or electrical pulse generator.

In embodiments, the controller is configured to apply radiofrequency drive signals to the acousto-optic device to produce the desired number of angularly deflected laser beams in the output laser beam, such as being configured to apply 3 or more radiofrequency drive signals, such as 4 or more radiofrequency drive signals, such as 5 or more radiofrequency drive signals, such as 6 or more radiofrequency drive signals, such as 7 or more radiofrequency drive signals, such as 8 or more radiofrequency drive signals, such as 9 or more radiofrequency drive signals, such as 10 or more radiofrequency drive signals, such as 15 or more radiofrequency drive signals, such as 25 or more radiofrequency drive signals, such as 50 or more radiofrequency drive signals and including being configured to apply 100 or more radiofrequency drive signals.

To produce an intensity profile of the angularly deflected laser beams in the output laser beam, the controller is configured to apply radiofrequency drive signals having an amplitude that varies such as from about 0.001 V to about 500 V, such as from about 0.005 V to about 400 V, such as from about 0.01 V to about 300 V, such as from about 0.05 V to about 200 V, such as from about 0.1 V to about 100 V, such as from about 0.5 V to about 75 V, such as from about 1 V to 50 V, such as from about 2 V to 40 V, such as from 3 V to about 30 V and including from about 5 V to about 25 V. Each applied radiofrequency drive signal has, in some embodiments, a frequency of from about 0.001 MHz to about 500 MHz, such as from about 0.005 MHz to about 400 MHz, such as from about 0.01 MHz to about 300 MHz, such as from about 0.05 MHz to about 200 MHz, such as from about 0.1 MHz to about 100 MHz, such as from about 0.5 MHz to about 90 MHz, such as from about 1 MHz to about 75 MHz, such as from about 2 MHz to about 70 MHz, such as from about 3 MHz to about 65 MHz, such as from about 4 MHz to about 60 MHz and including from about 5 MHz to about 50 MHz.

In certain embodiments, the controller has a processor having memory operably coupled to the processor such that the memory includes instructions stored thereon, which when executed by the processor, cause the processor to produce an output laser beam with angularly deflected laser beams having a desired intensity profile. For example, the memory may include instructions to produce two or more angularly deflected laser beams with the same intensities, such as 3 or more, such as 4 or more, such as 5 or more, such as 10 or more, such as 25 or more, such as 50 or more and including memory may include instructions to produce 100 or more angularly deflected laser beams with the same intensities. In other embodiments, the may include instructions to produce two or more angularly deflected laser beams with different intensities, such as 3 or more, such as 4 or more, such as 5 or more, such as 10 or more, such as 25 or more, such as 50 or more and including memory may include instructions to produce 100 or more angularly deflected laser beams with different intensities.

In certain embodiments, the controller has a processor having memory operably coupled to the processor such that the memory includes instructions stored thereon, which when executed by the processor, cause the processor to produce an output laser beam having increasing intensity from the edges to the center of the output laser beam along the horizontal axis. In these instances, the intensity of the angularly deflected laser beam at the center of the output beam may range from 0.1% to about 99% of the intensity of the angularly deflected laser beams at the edge of the output laser beam along the horizontal axis, such as from 0.5% to about 95%, such as from 1% to about 90%, such as from about 2% to about 85%, such as from about 3% to about 80%, such as from about 4% to about 75%, such as from about 5% to about 70%, such as from about 6% to about 65%, such as from about 7% to about 60%, such as from about 8% to about 55% and including from about 10% to about 50% of the intensity of the angularly deflected laser beams at the edge of the output laser beam along the horizontal axis. In other embodiments, the controller has a processor having memory operably coupled to the processor such that the memory includes instructions stored thereon, which when executed by the processor, cause the processor to produce an output laser beam having an increasing intensity from the edges to the center of the output laser beam along the horizontal axis. In these instances, the intensity of the angularly deflected laser beam at the edges of the output beam may range from 0.1% to about 99% of the intensity of the angularly deflected laser beams at the center of the output laser beam along the horizontal axis, such as from 0.5% to about 95%, such as from 1% to about 90%, such as from about 2% to about 85%, such as from about 3% to about 80%, such as from about 4% to about 75%, such as from about 5% to about 70%, such as from about 6% to about 65%, such as from about 7% to about 60%, such as from about 8% to about 55% and including from about 10% to about 50% of the intensity of the angularly deflected laser beams at the center of the output laser beam along the horizontal axis. In yet other embodiments, the controller has a processor having memory operably coupled to the processor such that the memory includes instructions stored thereon, which when executed by the processor, cause the processor to produce an output laser beam having an intensity profile with a Gaussian distribution along the horizontal axis. In still other embodiments, the controller has a processor having memory operably coupled to the processor such that the memory includes instructions stored thereon, which when executed by the processor, cause the processor to produce an output laser beam having a top hat intensity profile along the horizontal axis.

In embodiments, systems are configured to produce angularly deflected laser beams in the output laser beam that are spatially separated. Depending on the applied radiofrequency drive signals and desired irradiation profile of the output laser beam, the angularly deflected laser beams may be separated by 0.001 μm or more, such as by 0.005 μm or more, such as by 0.01 μm or more, such as by 0.05 μm or more, such as by 0.1 μm or more, such as by 0.5 μm or more, such as by 1 μm or more, such as by 5 μm or more, such as by 10 µm or more, such as by 100 µm or more, such as by 500 µm or more, such as by 1000 µm or more and including by 5000 µm or more. In some embodiments, systems are configured to produce angularly deflected laser beams in the output laser beam that overlap, such as with an adjacent angularly deflected laser beam along a horizontal axis of the output laser beam. The overlap between adjacent angularly deflected laser beams (such as overlap of beam spots) may be an overlap of 0.001 µm or more, such as an overlap of 0.005 µm or more, such as an overlap of 0.01 µm or more, such as an overlap of 0.05 µm or more, such as an overlap of 0.1 µm or more, such as an overlap of 0.5 µm or more, such as an overlap of 1 µm or more, such as an overlap of 5 µm or more, such as an overlap of 10 µm or more and including an overlap of 100 µm or more.

In some embodiments, systems include a flow cell configured to propagate the sample in the flow stream. Any convenient flow cell which propagates a fluidic sample to a sample interrogation region may be employed, where in some embodiments, the flow cell includes a proximal cylindrical portion defining a longitudinal axis and a distal frustoconical portion which terminates in a flat surface having the orifice that is transverse to the longitudinal axis. The length of the proximal cylindrical portion (as measured along the longitudinal axis) may vary ranging from 1 mm to 15 mm, such as from 1.5 mm to 12.5 mm, such as from 2 mm to 10 mm, such as from 3 mm to 9 mm and including from 4 mm to 8 mm. The length of the distal frustoconical portion (as measured along the longitudinal axis) may also vary, ranging from 1 mm to 10 mm, such as from 2 mm to 9 mm, such as from 3 mm to 8 mm and including from 4 mm to 7 mm. The diameter of the of the flow cell nozzle chamber may vary, in some embodiments, ranging from 1 mm to 10 mm, such as from 2 mm to 9 mm, such as from 3 mm to 8 mm and including from 4 mm to 7 mm.

In certain instances, the flow cell does not include a cylindrical portion and the entire flow cell inner chamber is frustoconically shaped. In these embodiments, the length of the frustoconical inner chamber (as measured along the longitudinal axis transverse to the nozzle orifice), may range from 1 mm to 15 mm, such as from 1.5 mm to 12.5 mm, such as from 2 mm to 10 mm, such as from 3 mm to 9 mm and including from 4 mm to 8 mm. The diameter of the proximal portion of the frustoconical inner chamber may range from 1 mm to 10 mm, such as from 2 mm to 9 mm, such as from 3 mm to 8 mm and including from 4 mm to 7 mm.

In some embodiments, the sample flow stream emanates from an orifice at the distal end of the flow cell. Depending on the desired characteristics of the flow stream, the flow cell orifice may be any suitable shape where cross-sectional shapes of interest include, but are not limited to: rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. In certain embodiments, flow cell of interest has a circular orifice. The size of the nozzle orifice may vary, in some embodiments ranging from 1 µm to 20000 µm, such as from 2 µm to 17500 µm, such as from 5 µm to 15000 µm, such as from 10 µm to 12500 µm, such as from 15 µm to 10000 µm, such as from 25 µm to 7500 µm, such as from 50 µm to 5000 µm, such as from 75 µm to 1000 µm, such as from 100 µm to 750 µm and including from 150 µm to 500 µm. In certain embodiments, the nozzle orifice is 100 µm.

In some embodiments, the flow cell includes a sample injection port configured to provide a sample to the flow cell. In embodiments, the sample injection system is configured to provide suitable flow of sample to the flow cell inner chamber. Depending on the desired characteristics of the flow stream, the rate of sample conveyed to the flow cell chamber by the sample injection port may be 1 µL/min or more, such as 2 µL/min or more, such as 3 µL/min or more, such as 5 µL/min or more, such as 10 µL/min or more, such as 15 µL/min or more, such as 25 µL/min or more, such as 50 µL/min or more and including 100 µL/min or more, where in some instances the rate of sample conveyed to the flow cell chamber by the sample injection port is 1 µL/sec or more, such as 2 µL/sec or more, such as 3 µL/sec or more, such as 5 µL/sec or more, such as 10 µL/sec or more, such as 15 µL/sec or more, such as 25 µL/sec or more, such as 50 µL/sec or more and including 100 µL/sec or more.

The sample injection port may be an orifice positioned in a wall of the inner chamber or may be a conduit positioned at the proximal end of the inner chamber. Where the sample injection port is an orifice positioned in a wall of the inner chamber, the sample injection port orifice may be any suitable shape where cross-sectional shapes of interest include, but are not limited to: rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion. In certain embodiments, the sample injection port has a circular orifice. The size of the sample injection port orifice may vary depending on shape, in certain instances, having an opening ranging from 0.1 mm to 5.0 mm, e.g., 0.2 to 3.0 mm, e.g., 0.5 mm to 2.5 mm, such as from 0.75 mm to 2.25 mm, such as from 1 mm to 2 mm and including from 1.25 mm to 1.75 mm, for example 1.5 mm.

In certain instances, the sample injection port is a conduit positioned at a proximal end of the flow cell inner chamber. For example, the sample injection port may be a conduit positioned to have the orifice of the sample injection port in line with the flow cell orifice. Where the sample injection port is a conduit positioned in line with the flow cell orifice, the cross-sectional shape of the sample injection tube may be any suitable shape where cross-sectional shapes of interest include, but are not limited to: rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. The orifice of the conduit may vary depending on shape, in certain instances, having an opening ranging from 0.1 mm to 5.0 mm, e.g., 0.2 to 3.0 mm, e.g., 0.5 mm to 2.5 mm, such as from 0.75 mm to 2.25 mm, such as from 1 mm to 2 mm and including from 1.25 mm to 1.75 mm, for example 1.5 mm. The shape of the tip of the sample injection port may be the same or different from the cross-section shape of the sample injection tube. For example, the orifice of the sample injection port may include a beveled tip having a bevel angle ranging from 1° to 10°, such as from 2° to 9°, such as from 3° to 8°, such as from 4° to 7° and including a bevel angle of 5°.

In some embodiments, the flow cell also includes a sheath fluid injection port configured to provide a sheath fluid to the flow cell. In embodiments, the sheath fluid injection system is configured to provide a flow of sheath fluid to the flow cell inner chamber, for example in conjunction with the sample to produce a laminated flow stream of sheath fluid surrounding the sample flow stream. Depending on the desired characteristics of the flow stream, the rate of sheath fluid conveyed to the flow cell chamber by the may be 25 µL/sec or more, such as 50 µL/sec or more, such as 75 µL/sec or more, such as 100 µL/sec or more, such as 250 µL/sec or more, such as 500 µL/sec or more, such as 750 µL/sec or more, such as 1000 µL/sec or more and including 2500 µL/sec or more.

In some embodiments, the sheath fluid injection port is an orifice positioned in a wall of the inner chamber. The sheath fluid injection port orifice may be any suitable shape where cross-sectional shapes of interest include, but are not limited to: rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. The size of the sample injection port orifice may vary depending on shape, in certain instances, having an opening ranging from 0.1 mm to 5.0 mm, e.g., 0.2 to 3.0 mm, e.g., 0.5 mm to 2.5 mm, such as from 0.75 mm to 2.25 mm, such as from 1 mm to 2 mm and including from 1.25 mm to 1.75 mm, for example 1.5 mm.

In some embodiments, systems further include a pump in fluid communication with the flow cell to propagate the flow stream through the flow cell. Any convenient fluid pump protocol may be employed to control the flow of the flow stream through the flow cell. In certain instances, systems include a peristaltic pump, such as a peristaltic pump having a pulse damper. The pump in the subject systems is configured to convey fluid through the flow cell at a rate suitable for detecting light from the sample in the flow stream. In some instances, the rate of sample flow in the flow cell is 1 µL/min (microliter per minute) or more, such as 2 µL/min or more, such as 3 µL/min or more, such as 5 µL/min or more, such as 10 µL/min or more, such as 25 µL/min or more, such as 50 µL/min or more, such as 75 µL/min or more, such as 100 µL/min or more, such as 250 µL/min or more, such as 500 µL/min or more, such as 750 µL/min or more and including 1000 µL/min or more. For example, the system may include a pump that is configured to flow sample through the flow cell at a rate that ranges from 1 µL/min to 500 µL/min, such as from 1 uL/min to 250 uL/min, such as from 1 uL/min to 100 uL/min, such as from 2 µL/min to 90 µL/min, such as from 3 µL/min to 80 µL/min, such as from 4 µL/min to 70 µL/min, such as from 5 µL/min to 60 µL/min and including from 10 µL/min to 50 µL/min. In certain embodiments, the flow rate of the flow stream is from 5 µL/min to 6 µL/min.

Systems also include one or more detectors for detecting light from a sample in a flow stream (e.g., in a flow cytometer). The detectors may be configured to detect side scattered light, forward scattered light, emitted light or combination thereof. Suitable light detecting protocols, include but are not limited to optical sensors or photodetectors, such as active-pixel sensors (APSs), avalanche photodiode, image sensors, charge-coupled devices (CODs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, light from the irradiated flow stream at the sample interrogation region of the particle sorting module is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors. In certain embodiments, light is measured with a charge-coupled device (CCD).

Systems may also include one or more optical adjustment components. For example, systems may include lens, mirrors, collimators, wavelength separators such as colored glass, bandpass filters, interference filters, dichroic mirrors, diffraction gratings, monochromators, etc. In certain embodiments, systems include a beam splitter and an optical inverter component, such as for inverting an output laser beam along a horizontal axis as described above. In certain embodiments, the detector is positioned apart in space from the sample in the flow stream and light from the sample in the flow stream is propagated to the detector through an optical relay system, such as with fiber optics or a free space light relay system. For example, the optical relay system may be a fiber optics light relay bundle and light is conveyed through the fiber optics light relay bundle to the detector. Any fiber optics light relay system may be employed to propagate light to the detector. In certain embodiments, suitable fiber optics light relay systems for propagating light to the detector include, but are not limited to, fiber optics light relay systems such as those described in U.S. Pat. No. 6,809,804, the disclosure of which is herein incorporated by reference. In other embodiments, the optical relay system is a free-space light relay system. The phrase "free-space light relay" is used herein in its conventional sense to refer to light propagation that employs a configuration of one or more optical components to direct light to the detector through free-space. In certain embodiments, the free-space light relay system includes a housing having a proximal end and a distal end, the proximal end being coupled to the detector. The free-space relay system may include any combination of different optical adjustment components, such as one or more of lenses, mirrors, slits, pinholes, wavelength separators, or a combination thereof. For example, in some embodiments, free-space light relay systems of interest include one or more focusing lens. In other embodiments, the subject free-space light relay systems include one or more mirrors. In yet other embodiments, the free-space light relay system includes a collimating lens. In certain embodiments, suitable free-space light relay systems for propagating light to the detector, but are not limited to, light relay systems such as those described in U.S. Pat. Nos. 7,643,142; 7,728,974 and 8,223,445, the disclosures of which is herein incorporated by reference.

In certain embodiments, the subject systems are flow cytometric systems employing the above described systems for producing an output laser beam having two or more angularly deflected laser beams (e.g., for irradiating a sample in a flow stream) with a predetermined intensity profile. Suitable flow cytometry systems and methods for analyzing samples include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem*. January; 49(pt 1):17-28; Linden, et. al., *Semin Throm Hemost*. 2004 October; 30(5):502-11; Alison, et al. *J Pathol*, 2010 December; 222(4):335-344; and Herbig, et al. (2007) *Crit Rev Ther Drug Carrier Syst*. 24(3): 203-255; the disclosures of which are incorporated herein by reference. In certain instances, flow cytometry systems of interest include BD Biosciences FACSCanto™ flow cytometer, BD Biosciences FACSVantage™, BD Biosciences FACSort™, BD Biosciences FACSCount™, BD Biosciences FACScan™, and BD Biosciences FACSCalibur™ systems, a BD Biosciences Influx™ cell sorter, BD Biosciences Jazz™ cell sorter and BD Biosciences Aria™ cell sorter or the like.

In certain embodiments, the subject systems are flow cytometer systems which incorporate one or more components of the flow cytometers described in U.S. Pat. Nos. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040; 5,643,796; 5,700,692; 6,372,506; 6,809,804; 6,813,017; 6,821,740; 7,129,505; 7,201,875; 7,544,326; 8,140,300; 8,233,146; 8,753,573; 8,975,595; 9,092,034; 9,095,494 and 9,097,640; the disclosures of which are herein incorporated by reference.

As summarized above, the present invention relates generally to methods and systems for performing flow cytometry. As discussed in more detail below (in particular with reference to FIGS. 1-15), in some embodiments, an acousto-optic deflector is used to generate a plurality of beamlets, in response to application of a plurality of radiofrequency signals to the deflector, which collectively form an excitation beam. The applied radiofrequency signals can be adjusted so as to vary certain characteristics of the beamlets and hence the respective ones of the resultant excitation beam. For example, as discussed in more detail below, the powers of the radiofrequency signals can be adjusted so as to vary the intensity of the excitation beam along its horizontal dimension. Such variation can be used, for example, to ensure a substantially uniform optical response from equivalent particles passing through different portions of the beam. In some embodiments, the frequencies of the applied signals can be adjusted to spatially move the excitation beam so as to track a sample stream flowing through a flow cell of a flow cytometer.

FIG. 1 schematically depicts a flow cytometry system 10 according to an embodiment of the present invention, which includes a laser source 12 for generating a laser beam LB. By way of example, the laser beam can have a frequency in a range of about 1000 THz to about 300 THz, though other frequencies can also be employed. The beam diameter of the laser beam (e.g., the beam waist when a Gaussian laser beam is employed) can be, for example, in a range of about 0.1 mm to about 10 mm. Without any loss of generality, in this embodiment, the laser is assumed to be operating in the $TEM_{00}$ mode to generate a Gaussian beam. In other embodiments, other beam intensity profiles may be employed.

A mirror 14 directs the laser radiation to an acousto-optic deflector 16. A radiofrequency (RF) generator 18, e.g., a direct digital synthesizer, operating under the control of a controller 20, can apply a plurality of radio-frequency drive signals concurrently to the acousto-optic deflector 16 so as to generate a plurality of angularly separated beamlets that can collectively form an excitation beam. The drive signals may be frequency shifted relative to one another by a frequency in a range of about 10 MHz to about 250 MHz, e.g., in a range of about 50 MHz to about 150 MHz. In some embodiments, the radiofrequency shift between adjacent drive signals can be in a range of about 0.1 MHz to about 4 MHz. In many embodiments, the RF drive signals are equally spaced in frequency and hence are referred to herein as an RF frequency comb.

Figure 2:
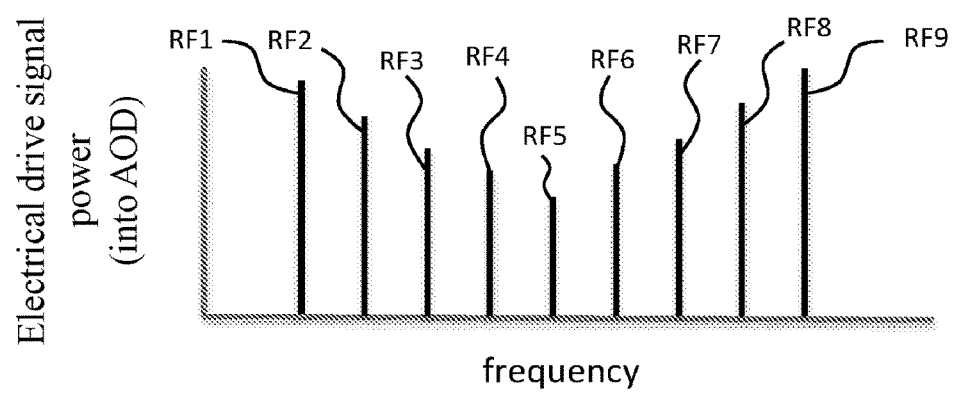
FIG. 2 schematically depicts a plurality of RF drive signals generated by an RF generator for application to an acousto-optic deflector of the system of FIG. 1.

By way of example, as shown schematically in FIG. 2, the RF generator can apply a plurality of drive signals RF1, . . . , RF8, to the acousto-optic deflector. The interaction of the laser beam with each of the RF drive signals can cause diffraction of the laser beam into multiple diffraction orders. As shown in FIG. 1, in this embodiment, the acousto-optic deflector is configured such that for each drive signal, the beamlet corresponding to the −1 diffraction order propagates toward a convergent lens 22 (the respective zeroth order beamlet is captured by a beam stop).

Figure 3:
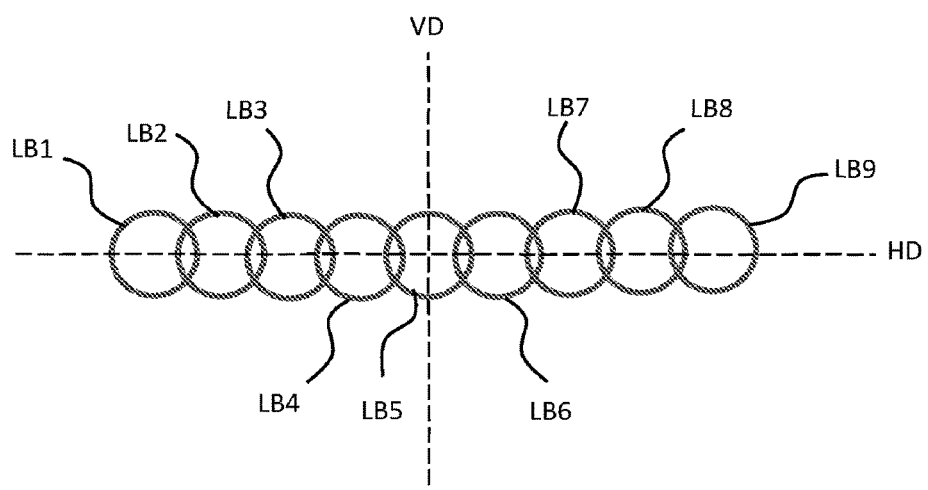
FIG. 3 schematically depicts a plurality of beamlets generated in response to the application of the RF drive signals shown in FIG. 2 to the acousto-optic deflector.

The beamlets associated with the drive signals are angularly separated from one another, and are in some cases partially overlapping. For example, FIG. 3 schematically depicts a plurality of such beamlets BL1, . . . , BL9, each of which is associated with one of the drive signals RF1, . . . , RF8 shown in FIG. 2. In this example, the adjacent beamlets are partially spatially overlapping and the beamlets collectively form an excitation beam 24, as shown in FIG. 1, which has an elongated extent along one dimension, which is assumed to be the horizontal direction in this embodiment. By way of example, the ratio of the beam's extent along the horizontal direction relative to the vertical direction (e.g., based on full width at half maximum intensity) can be greater than about 4.

Each of the beamlets is frequency-shifted relative to the frequency of the laser beam (LB) by an offset frequency corresponding to the RF frequency of the drive signal associated with that beamlet. Further, the intensities of the beamlets can vary based on the electrical powers of the drive signals. For example, the drive signals shown in FIG. 2 show a maximum power for the drive signals RF1 and RF8 and a minimum power for the drive signal RF5. More specifically, in this example, the power of the drive signals decreases linearly from that of RF1 to that of RF5 and increases linearly from RF5 to RF8. This variation in the powers of the drive signals causes a respective variation of the intensities of the beamlets generated by those drive signals along the horizontal direction. Such variations are superimposed on the initial intensity profile of the laser beam along the horizontal direction to provide an excitation beam exhibiting a desired intensity variation along the horizontal dimension.

Figure 4:
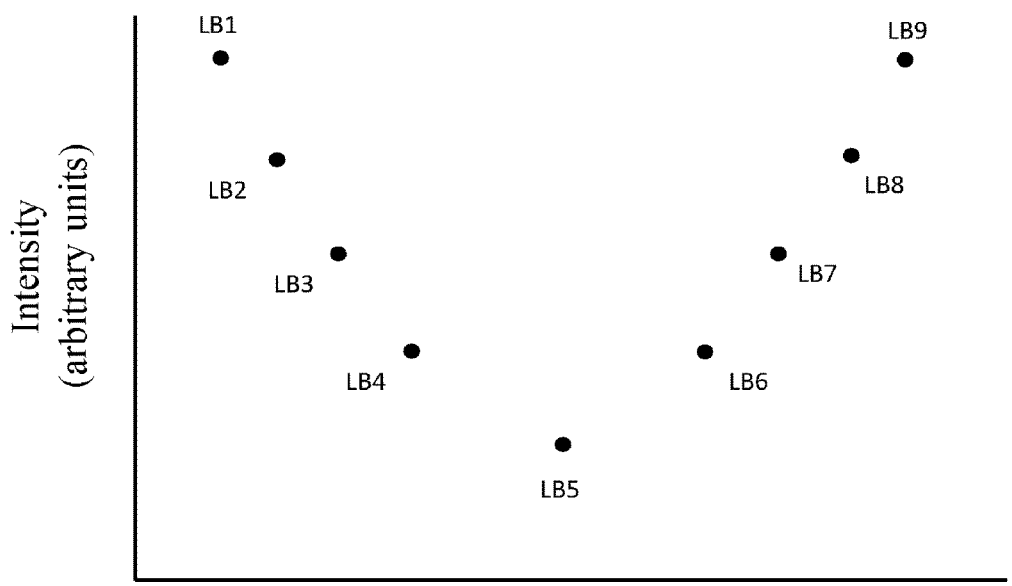
FIG. 4 schematically depicts a hypothetical intensity variation of an excitation beam formed collectively by the beamlets depicted in FIG. 3.
Figure 5:
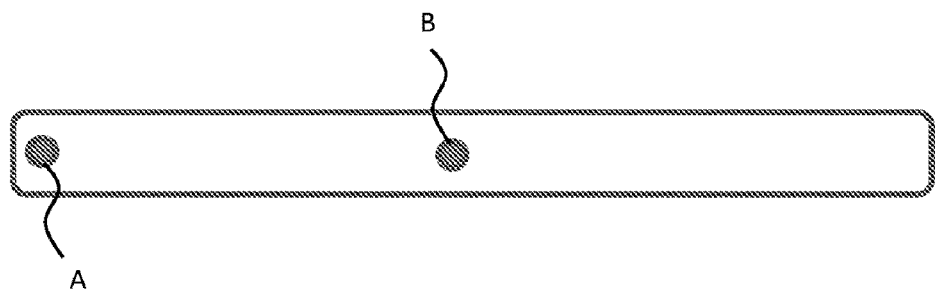
FIG. 5 schematically depicts two exemplary particles passing through different portions of the excitation beam generated by the beamlets shown in FIG. 3, thereby being exposed to different excitation intensities.

For example, with reference to FIG. 4, in this embodiment, the intensities of the beamlets BL1, . . . , BL9, shown schematically in FIG. 3 vary along the horizontal direction (depicted schematically by the dashed line labeled HD) linearly from a maximum intensity for the beamlet BL1 to a minimum intensity for the beamlet BL5, and increases linearly from the intensity of the beamlet BL5 to that of beamlet BL9. This variation of the intensity of the beamlets in this example gives rise to an intensity-varied excitation beam that has a higher intensity at its horizontal edges than at its center. In this example, the beamlets can have a Gaussian intensity distribution along the vertical direction (depicted by the solid line VD), though other intensity distributions can also be used.

The controller 20 can adjust the powers of the drive signals applied to the acousto-optic deflector 16 (by adjusting their amplitudes) so as to obtain a variety of different intensity variations across the horizontal dimension of the resultant excitation beam. In some cases, such as the above example, the controller 20 can adjust the amplitudes of the drive signals (and consequently the power associated with each drive signal) such that the excitation beam has a maximum intensity at its horizontal edges and a minimum intensity at its center. In other embodiments, the amplitudes of the drive signals can be adjusted to obtain other intensity distributions across the horizontal dimension of the excitation beam. For example, in some cases, the intensity variation across the excitation beam can be characterized by an oscillatory variation. In some embodiments, the amplitudes of the RF signals applied to the acousto-optic deflector can vary in a range of about 0.1 volts to about 40 volts. In some embodiments, the variation of the amplitudes of the drive signals (and consequently the variation of the powers of the drive signals) can give rise to a maximum optical intensity variation along at least one dimension of the excitation beam (chosen as the horizontal dimension in this embodiment) in a range of about 0.1% to about 99%, e.g., in a range of about 5% to about 90%, or in a range of about 10% to about 80%, or in a range of about 20% to about 70%. Thus, a particular desired intensity profile of the excitation beam along the horizontal dimension can be digitally "dialed in" via variation of the electrical powers associated with the different drive signals applied to acousto-optic deflector.

As discussed in more detail below, in some embodiments, such intensity variation allows for a greater excitation of the particles (e.g., cells) flowing through the edges of the excitation beam to counter the lower collection efficiency for radiation (e.g., fluorescence emission) emanating from those particles in response to excitation in order to detect a substantially uniform optical response from the illuminated equivalent particles across a larger spatial extent in the flow cell than is possible using a conventional Gaussian or flat-top profile excitation laser spot.

Referring again to FIG. 1, in this embodiment, the excitation beam 24 is focused by the convergent lens 22 into a flow cell 26 to illuminate a plurality of particles flowing through the cell. In this exemplary embodiment, the particles are assumed to be flowing out of plane of the figure along a vertical direction. The illuminated particles can emit radiation (e.g., via fluorescence and/or scattering), which can be detected and analyzed, as discussed in more detail below.

In this embodiment, the forward scattered radiation is focused by a lens 28 onto a photodetector 30 and is detected. The excitation beam passing through the flow cell without scattering is captured by a beam stop 34. A bandpass filter 32 is placed in front of the photodetector 30 to allow the transmission of the excitation laser wavelength and to reject other wavelengths. An analyzer 36 can receive the signals generated by the photodetector 30 and can process those signals to generate, for example, a forward-scatter signal from the sample.

In an orthogonal direction to the forward scattering direction, the radiation emanating from the particles (e.g., fluorescent and/or scattered radiation) can be collected by an objective lens 38 and focused via a lens 40 onto a multi-mode optical fiber 42, which extends from a proximal end (PE) to a distal end (DE). More specifically, the proximal end (PE) of the optical fiber 42 is positioned in proximity of the focal plane of the lens 40 so as to efficiently receive the radiation (e.g., scattered and/or fluorescent radiation). An outcoupling lens 44, coupled to the distal end (DE) of the optical fiber 42, collimates the radiation exiting the fiber.

The collimated radiation is then detected by a plurality of photomultiplier tubes 46, 48, 50, and 52. More specifically, a dichroic mirror 54 reflects a portion of the radiation onto the photomultiplier tube 46 and allows passage of another portion of the radiation to a downstream dichroic mirror 56, which in turn reflects a portion of the received radiation onto the photomultiplier 50 and allows passage of another portion of the radiation to another dichroic mirror 58, which in turn reflects a portion of the received radiation onto the photomultiplier 48 and allows the passage of the remainder of the radiation to the photomultiplier tube 53. In this embodiment, a plurality of bandpass filters 46a, 48a, 50a and 52a are placed, respectively, in front of the photomultipliers 46, 48, 50 and 52.

The bandpass filters can be selected for a variety of different purposes. For example, in some embodiments, at least one of the bandpass filters can allow transmission of the laser excitation wavelength while rejecting other wavelengths so as to facilitate obtaining a side scatter signal from the sample. Further, in some embodiments, one or more of the bandpass filters can be selected to allow passage of fluorescent radiation by a fluorophore while substantially blocking other radiation. In some cases, different bandpass filters, each allowing transmission of fluorescent radiation corresponding to a different fluorophore, are used so as to allow concurrent detection of fluorescent radiation emitted by a plurality of fluorophores associated with a sample flowing through the flow cell. The photomultiplier tubes 46, 48, 50, and 52 generate signals in response to the detection of the radiation incident thereon. The analyzer 36 receives these signals and processes them to generate, for example, side-scatter and/or fluorescence data from the sample. This data can be created, for example, by analyzing the height, width, and area of the electronic pulses output by each photomultiplier tube.

By way of example, the excitation beam can excite one or more fluorophores associated with a sample flowing through the flow cell. The sample can include, for example, a flowing fluid in which a plurality of cells are entrained. In some cases, the cells can be labeled with one or more fluorescent markers (fluorophores). Some examples of fluorescent markers include, without limitation, fluorescent proteins (e.g., GFP, YFP, RFP), antibodies labeled with fluorophores (e.g., fluorescein isothiocyanate) (FITC), phycoerythrin (PE), allophycocyanin (APC)), nucleic acid stains (e.g., 4',6-diamidino-2-phenylindole (DAPI), SYTO16, propidium iodide (PI)), cell membrane stains (e.g., FMI-43), and cell function dyes (e.g., Fluo-4, Indo-1). In other cases, endogenous fluorophores present in cells can be employed to elicit fluorescent radiation from the cells. Such exogenous or endogenous fluorophores undergo electronic excitation in response to the illuminating radiation and emit fluorescent radiation (typically at a lower frequency than the excitation frequency), which is collected and analyzed.

As noted above, in this embodiment, the excitation beam exhibits an intensity variation along its horizontal dimension characterized by a higher intensity at the edges and a lower intensity at the center of the beam. Consequently, particles passing through different portions of the excitation beam are exposed to different excitation intensities. For example, as shown schematically in FIG. 5, a particle A (e.g., a cell) passing through a horizontal edge of the beam is exposed to a higher radiation intensity than a particle B passing through the center of the beam. In some embodiments, such intensity variation can be designed to substantially compensate for a lower collection efficiency, e.g., in the orthogonal direction (which is also described in some cases as a "90 degree collection geometry"), associated with radiation emanating from particles passing through the edges of the excitation beam, rather than its center. Further, in some cases, such intensity variation can ameliorate uneven excitation of the particles due to, for example, a lower beam intensity at the edges of the beam. For example, in a conventional system in which the excitation beam exhibits a Gaussian intensity distribution in the horizontal direction, the particles passing through the horizontal edges of the beam are exposed to a lower radiation intensity. This can in turn result in a lower intensity of the radiation (e.g., scattered and/or fluorescence radiation) emanating from such particles in response to interaction with the excitation beam. Further, the efficiency of the collection of the radiation emanating from the particles is generally uneven characterized by a lower collection efficiency for radiation emanating from those particles that pass through the edges of the beam. These factors can result in an uneven optical sensitivity as a function of the horizontal location (herein referred to as z position) at which a particle passes through the beam.

Figure 6A:
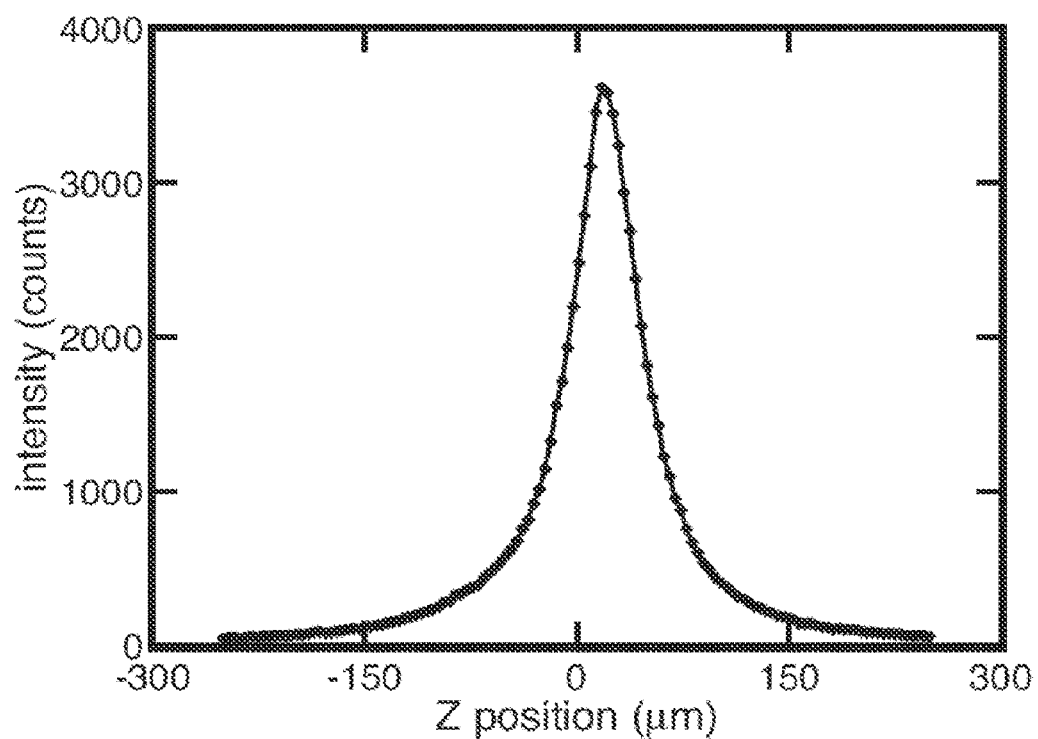
FIG. 6A is a schematic graph representing a hypothetical intensity of radiation detected from particles passing through an excitation beam having a Gaussian intensity distribution along both the horizontal and vertical directions.
Figure 6B:
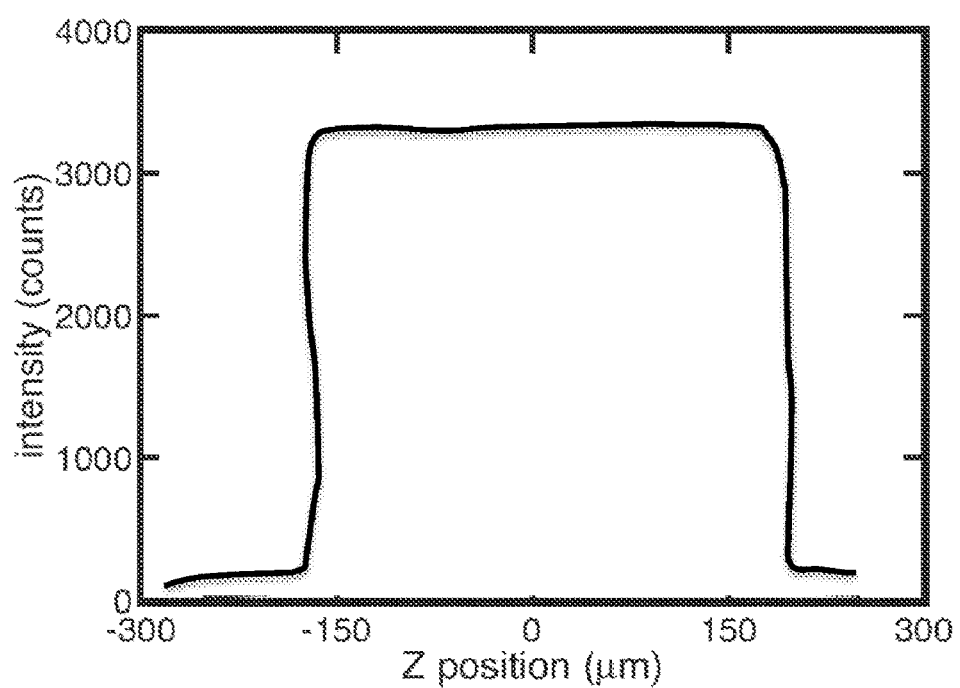
FIG. 6B schematically depicts a substantially uniform optical sensitivity as a function of horizontal positions of the particles along a hypothetical excitation beam according to the embodiment if the invention.

By way of example, FIG. 6A schematically depicts a graph representing a hypothetical intensity of detected radiation from particles passing through an excitation beam characterized by a Gaussian intensity distribution along the horizontal direction as a function of the horizontal locations of the particles along the beam. The graph shows a non-uniform optical sensitivity characterized by a greater sensitivity for particles passing through the center of the beam relative to those passing through the horizontal edges of the beam. In contrast, FIG. 6B presents a hypothetical intensity of radiation detected from particles after the intensity of the excitation beam is adjusted using, e.g., a RF comb as shown in FIG. 2. FIG. 6B depicts a substantially uniform optical sensitivity as a function of the horizontal excitation positions of the particles. In particular, the higher intensity at the horizontal edges of the beam can compensate for lower detection efficiency for detecting radiation emanating from those particles that pass through the horizontal edges of the beam. For example, in some embodiments, the optical detection sensitivity can vary by less than about 0.1% for equivalent particles passing through different portions of the excitation beam.

Figure 7:
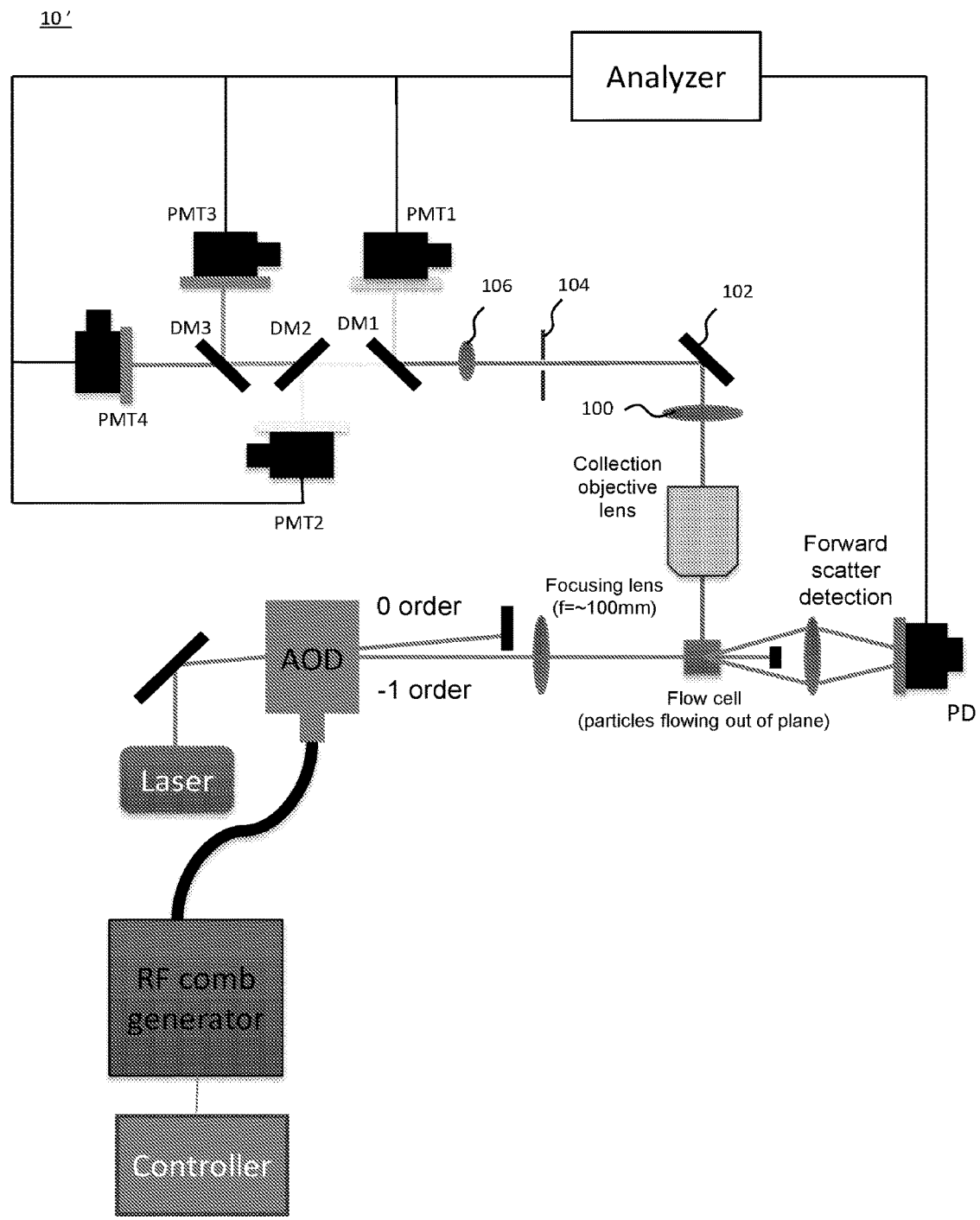
FIG. 7 schematically depicts a flow cytometer according to another embodiment of the invention.

In some embodiments, rather using a multi-mode optical fiber in the orthogonal detection arm, free space propagation of radiation emanating from a sample can be used to direct the radiation to the photomultiplier tubes. By way of example, FIG. 7 schematically depicts a flow cytometry system 10' according to such an embodiment that is similar to the flow cytometry system 10 discussed above except that it employs free space optical detection of the radiation emanating from the sample in the orthogonal direction. More specifically, in this embodiment, the objective lens 38 collects radiation (e.g., fluorescence and/or scattered radiation) emanating from a sample passing through the excitation beam and a lens 100 focuses the beam via reflection by a mirror 102 onto a pinhole 104. A beam emerging from the pinhole is collimated by a lens 106 and the collimated beam is directed to the photomultiplier tubes 46, 48, 50, and 52 in a manner discussed above. Similar to the previous embodiments, the forward scattered radiation can be focused by the lens 28 onto the photodetector 30. The analyzer 36 can receive the signals generated by the photodetector 30 and the photomultiplier tubes 46, 48, 50, and 52 and analyze those signals as discussed above.

In another aspect, the RF drive signals applied to the acousto-optic deflector can be adjusted so as to vary the horizontal extent (width) of the excitation beam. By way of example, the controller 20 can change the number of the drive signals applied to the acousto-optic deflector in order to widen or shorten the horizontal extent of the beam. Using a variable width RF frequency comb to excite a sample core stream at different flow rates, the excitation beam (the laser spot) can be concentrated on the sample core without wasting laser power by spreading it over a larger area to accommodate high sample flow rates and larger sample cores, as is done in conventional systems.

Figure 8A:
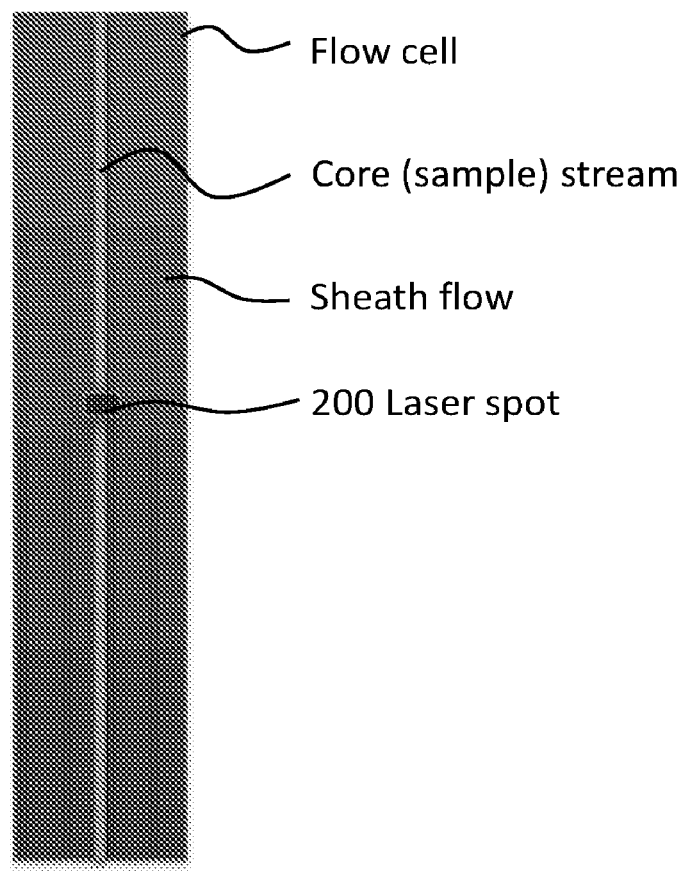
FIG. 8A schematically shows an excitation beam according to an embodiment of the invention.
Figure 8B:
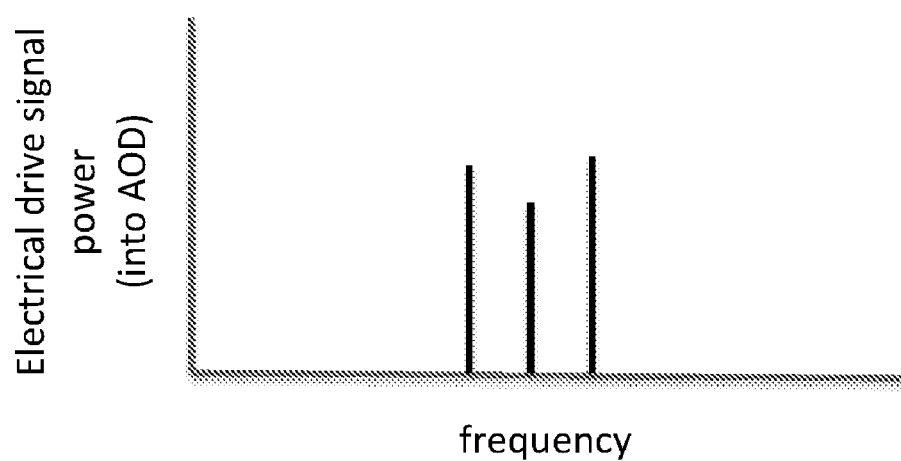
FIG. 8B schematically depicts hypothetical drive signals used to form the excitation beam depicted in FIG. 8A.

By way of illustration, FIG. 8A shows an excitation beam 200 (herein also referred to as laser spot) generated by applying three RF drive signals (schematically depicted in FIG. 8B) to the acousto-optic deflector 16. The width of the laser spot is relatively small, and hence is suitable for illuminating a relatively narrow core sample stream, e.g., a core sample stream flowing a relatively slow sample flow rate through the flow cell, e.g., at a rate in a range of about 1 microliter per minute to about 10 microliters per minute with a spatial extent of about 2 micrometers in diameter to about 10 micrometers in diameter.

Figure 9A:
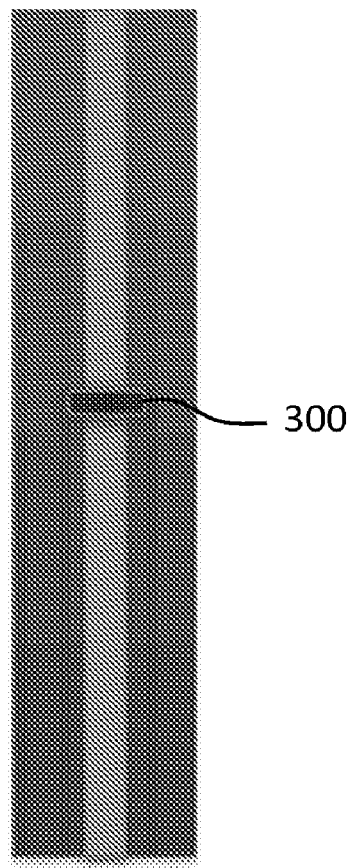
FIG. 9A schematically shows an excitation beam having a wider width relative to the excitation beam depicted in FIG. 8A.
Figure 9B:
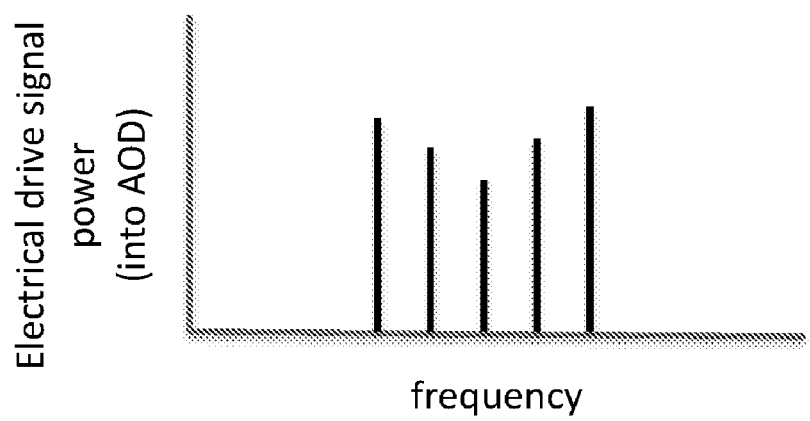
FIG. 9B schematically depicts hypothetical drive signals used to form the excitation beam depicted in FIG. 9A.
Figure 10A:
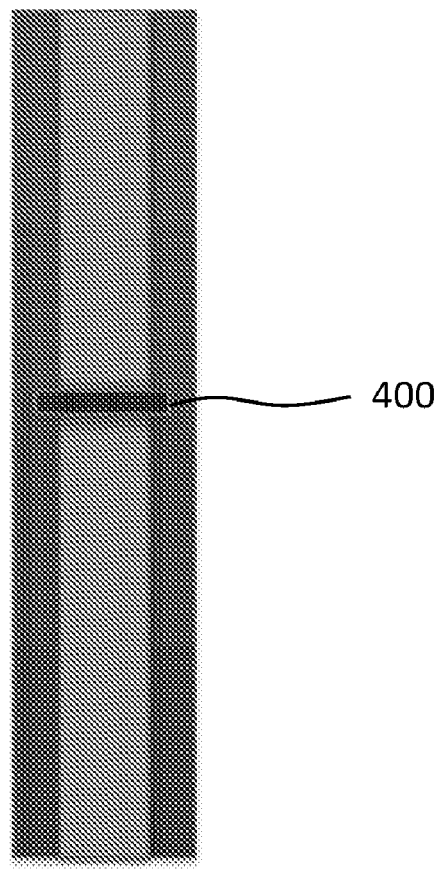
FIG. 10A schematically depicts an excitation beam having a wider width relative to the excitation beam depicted in FIG. 9A.
Figure 10B:
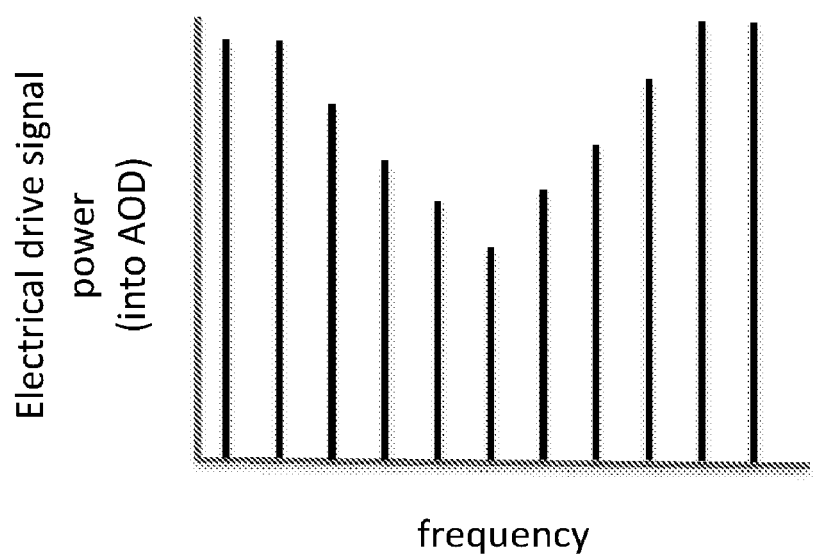
FIG. 10B schematically depicts hypothetical drive signals used to form the excitation beam depicted in FIG. 10A.

In contrast, FIG. 9A shows a laser spot 300 generated by concurrent application of six RF drive signals, as shown schematically in FIG. 9B, to the acousto-optic deflector, thus resulting a wider laser spot (i.e., an excitation beam having a larger horizontal extent). This laser beam is more suitable for illuminating a wider core sample stream, e.g., a core sample stream associated with a medium flow rate of a sample through the flow cell, e.g., a flow rate in a range of about 10 microliters per minute to about 50 microliters per minute. FIG. 10A shows a core stream associated with a high sample flow rate, e.g., a flow rate in a range of about 50 microliters per minute to about 1000 microliters per minute, and having a wider width. In this cases, a laser spot 400 for illuminating the core stream is generated via application of eleven RF drive signals (shown schematically in FIG. 10B) to the acousto-optic deflector 16, thereby having a greater horizontal extent that more closely matches the width of the sample stream.

In this manner, the use of the drive signals to adjust the size of the excitation beam, and in particular its horizontal extent, allows adapting the excitation beam to different flow rates of the sample through the flow cell. In some embodiments, the width of the excitation beam can be varied by at least about 1000% (i.e., a 10× change from the smallest to largest), for example, in a range of about 200% to about 500%. This adaptive illumination enables the use of lower power lasers to achieve higher illumination intensities on smaller sample core streams when desired, thus reducing the requirement for high-powered lasers in flow cytometers according to embodiments of the present teachings.

Further, in each of these examples, the powers of the applied RF drive signals can be adjusted in a manner discussed above so as to modulate the intensity of the excitation beam such that it has a greater intensity at its horizontal edges relative to its center.

In another aspect, the RF drive signals can be used to adjust the spatial position of the laser excitation spot to track the sample core stream. For example, with reference to any of FIG. 1 or 7, if a sample core stream spatially drifts over time as it flows through the flow cell, such drifts may be detected by the analyzer 36 through, e.g., a loss of fluorescence sensitivity or resolution. In such a case, the controller 20 can receive a signal from the analyzer indicative of the drift of the core stream. The controller can in turn cause the RF generator to adjust the absolute frequency of the drive signals, e.g., by digitally adjusting the frequencies directly or by scanning the clock frequency of the RF comb generator, so as to spatially move the beamlets and hence the excitation laser spot in order to track the sample core stream.

Figure 11:
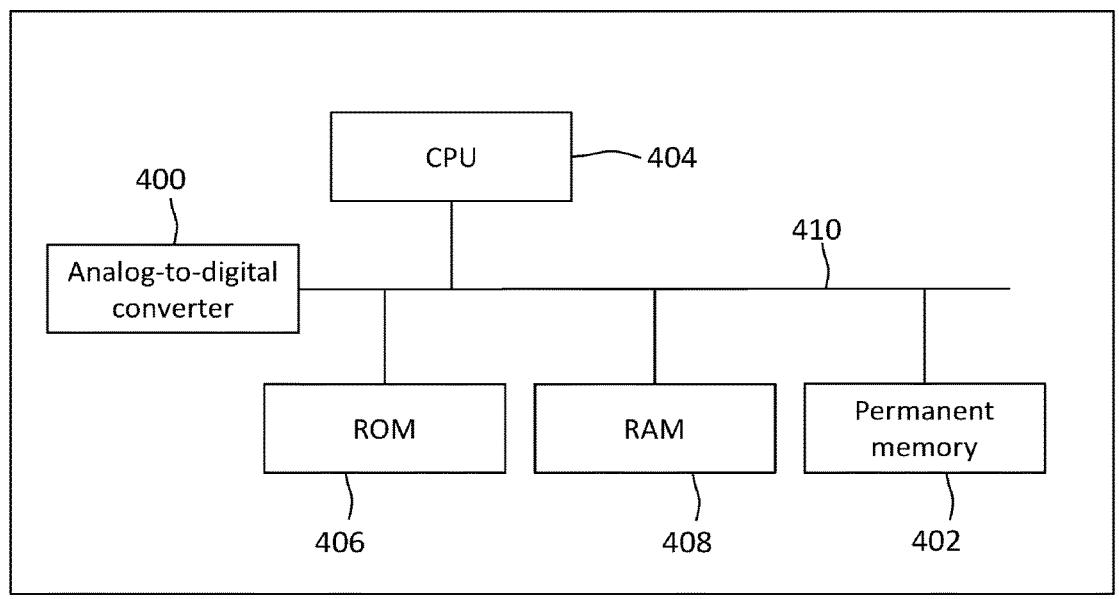
FIG. 11 schematically depicts an exemplary implementation of an analyzer used in various embodiments of the invention.

With reference to FIGS. 1 and 7, the controller 20 and the analyzer 36 can be implemented in a variety of different ways using known components and techniques. For example, any of the controller and the analyzer can be implemented in hardware, firmware and/or software using techniques known in the art and in accordance with the present teachings. By way of example, FIG. 11 schematically depicts such an implementation of the analyzer 36 in which an analog-to-digital converter 400 receives the signal(s) generated by the photodetector 30 and/or one or more the photomultiplier tubes 46, 48, 50, and 52. The signal(s) can be stored, for example, in a permanent memory 402. A central process unit (CPU) 404 can control the operation of the analyzer. The analyzer also includes ROM (read only memory) 406 and RAM (random access memory) 408. A communications bus 410 facilitates communication among various components of the analyzer, including communications between the CPU 404 and other components. The memory modules can be used to store instructions for analyzing the received signals. For example, in some embodiments, instructions for processing the received data can be stored in the ROM 406. The CPU can employ those instructions to operate on the digitized received signals to generate, e.g., height, width, and area measurements for the signals detected from the sample. The CPU can provide for the storage of processed signal(s) in the permanent memory 402. In addition, in some embodiments, a field-programmable gate array (FPGA) can be employed, instead of a CPU, to perform these calculations.

Figure 12:
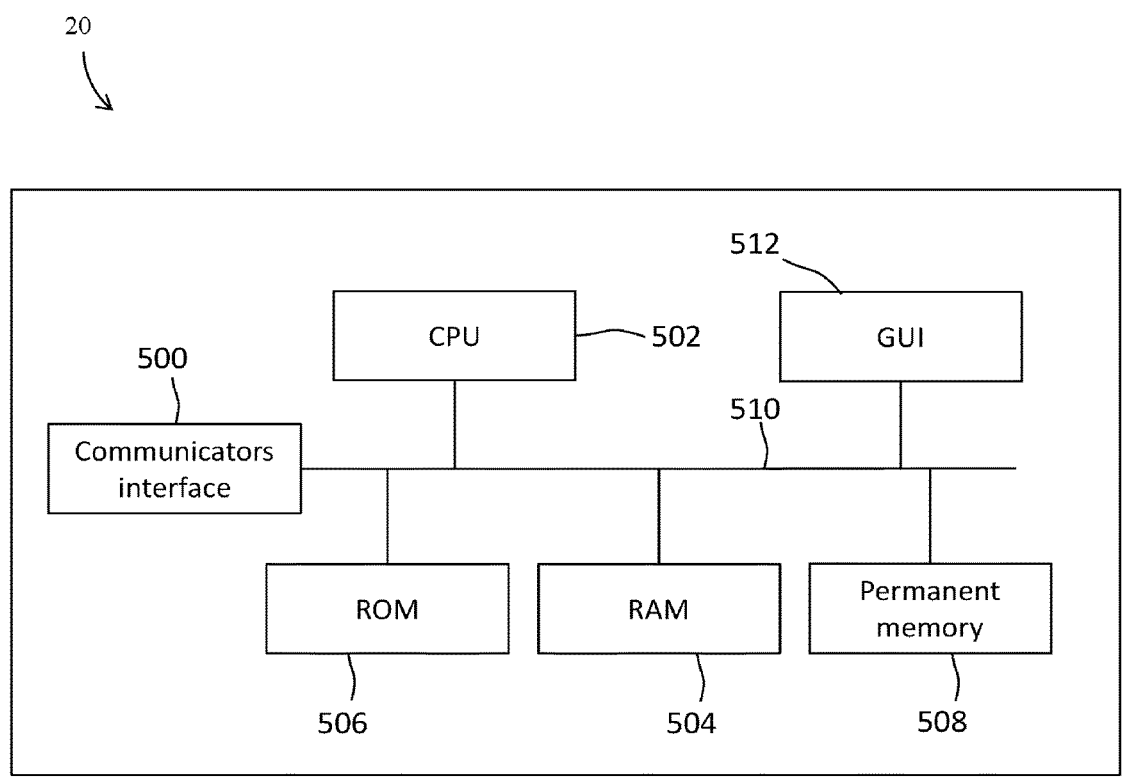
FIG. 12 schematically depicts an exemplary implementation of a controller used in various embodiments of the invention.

By way of further illustration, FIG. 12 schematically depicts an exemplary implementation of the controller 20. In this implementation, the controller 20 includes a communications interface 500 for communicating with the RF generator 18 to send commands to the generator and receive data therefrom. The controller can also communicate with the analyzer through the communications interface. By way of example, as discussed above, in some cases the controller can receive instructions from the analyzer, in response to variations in the intensity of fluorescence radiation detected from a sample, to cause the RF generator to vary the drive signals to spatially move the laser spot, thereby tracking the sample stream.

The controller 20 further includes a central processing unit (CPU) 502 that controls operation of the controller, RAM 504, ROM 506 and permanent memory 508. A communications bus 510 facilitates communication among different components of the controller. In this implementation, the controller further includes a graphical user interface (GUI) 512 that allows a user to interact with the controller, e.g., to configure the controller to instruct the RF generator to apply a desired pattern of drive signals to the acousto-optic deflector. In some embodiments, instruction data for performance of certain tasks by the controller, e.g., instructing the analyzer to vary the drive signal in response to changes in fluorescence intensity, can be stored in the ROM 506, which can be accessed by the CPU.

In another aspect, methods and systems are disclosed that employ beat frequency encoding of particle positions as they interact with a laser excitation beam. Such frequency encoding of the particle positions can be used in conjunction with equalized RF frequency combs to enable, for example, equalization of forward scatter signals.

Figure 13:
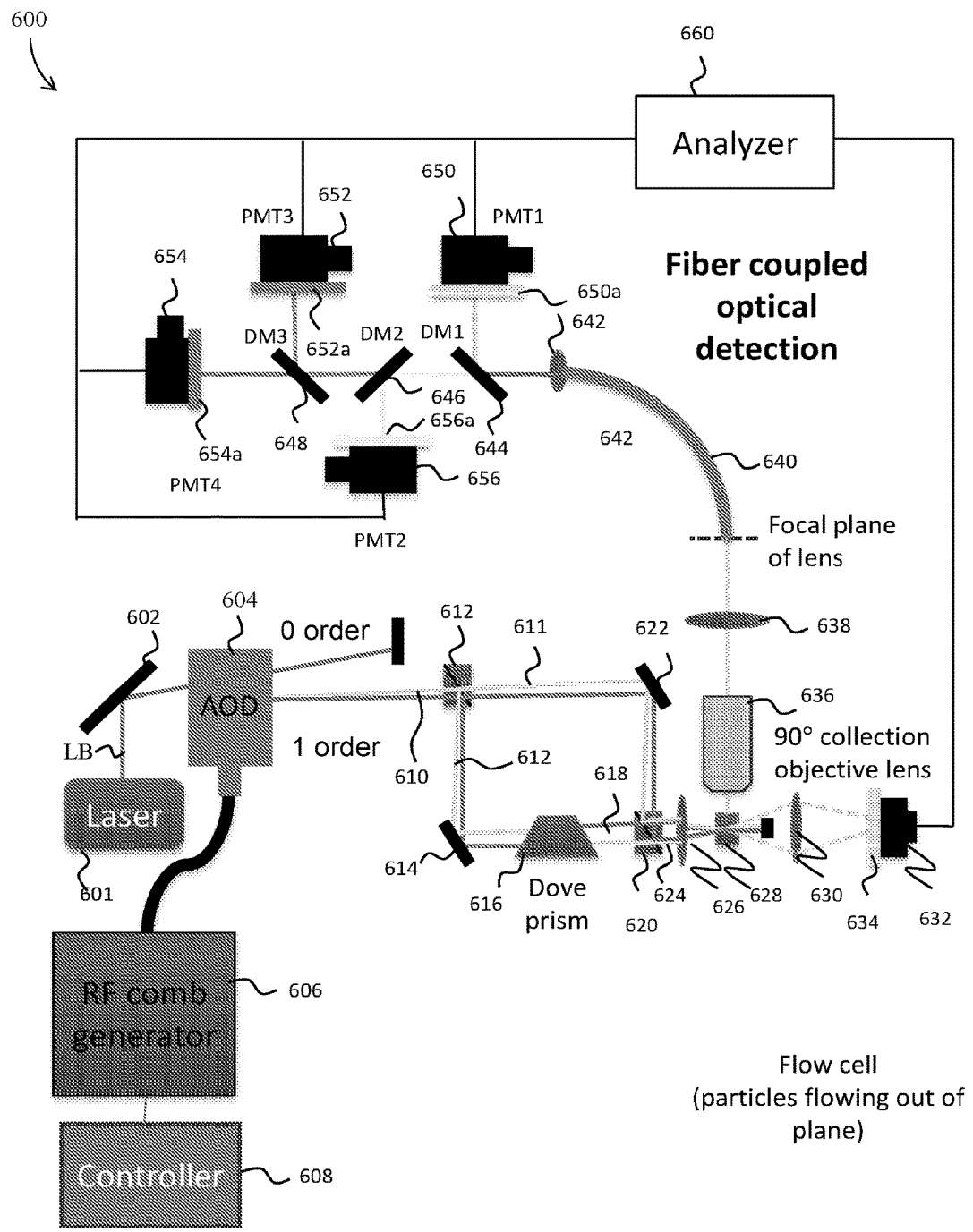
FIG. 13 schematically depicts a flow cytometer according to another embodiment of the invention.

By way of example, FIG. 13 schematically depicts a flow cytometry system 600 according to another embodiment of the present teachings, which includes a laser 601 for generating a laser radiation beam LB, which is received by an acousto-optic deflector 604 via reflection by a mirror 602. An RF comb generator 606 operating under the control of a controller 608 can apply RF drive signals to the acousto-optic deflector. As in the previous embodiments, the RF generator 606 can concurrently apply a plurality of RF drive signals to the acousto-optic deflector as to generate a plurality of beamlets, e.g., each corresponding to the −1 diffraction order of the interaction of the laser beam with radiofrequency oscillations generated by one of the drive signals.

Figure 14A:
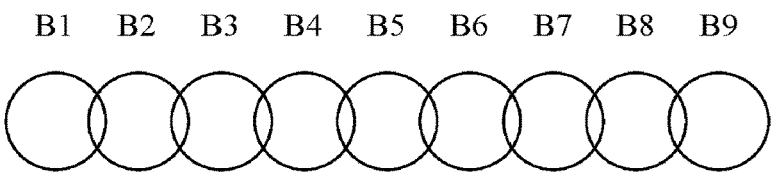
FIG. 14A schematically depicts a plurality of beamlets collectively forming a beam in the flow cytometer system of FIG. 13.

FIG. 14A schematically depicts such a plurality of beamlets B1, . . . , B9, which are partially spatially overlapping, and collectively form a laser excitation beam 610 (shown in FIG. 13). Similar to the previous embodiments, the powers of the RF drive signals can be adjusted so as to impart an intensity variation across the beamlets that form the excitation beam. By way of example, in this embodiment, the RF drive signals can have a variation in RF power shown schematically in FIG. 10B discussed above in connection with the previous embodiment, which can result in an intensity variation across the laser excitation beam along the horizontal dimension.

Each beamlet B1, . . . , B9 has an optical frequency that is shifted relative to the optical frequency of the excitation beam LB by the frequency of the drive signal associated with that beamlet. Thus, the beamlets B1, . . . , B9 can have optical frequencies $f_1, \ldots, f_9$, respectively, each of which is shifted by the RF comb spacing relative to the frequency ($f_0$) of the laser beam LB. Thus, the beamlets B1, . . . , B9 are frequency-shifted relative to one another by the frequency spacing of the RF comb, e.g., a frequency shift in a range of about 10 MHz to about 250 MHz, e.g., in a range of about 50 MHz to about 150 MHz, or in a range of about 0.1 MHz to about 4 MHz. In this case, the maximum optical frequency shift among the beamlets is $f_9$-$f_1$.

Figure 14B:
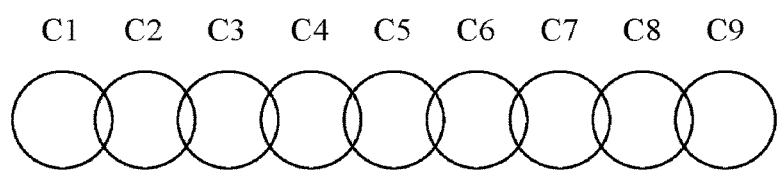
FIG. 14B shows one of the two beam obtained by splitting the beam depicted in FIG. 14A.
Figure 14C:
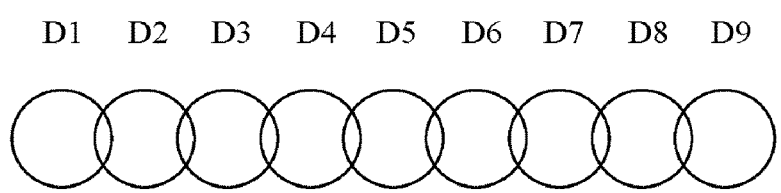
FIG. 14C shows the other the two beams obtained by splitting the beam depicted in FIG. 14B.

A beam splitter 612 receives the excitation beam 610 composed of the plurality of the beamlets B1, . . . , B9 and splits the beam into two propagating beams 611 and 612, each of which is a copy of the beam 612 at a lower intensity. As shown in FIGS. 14B and 14C, each of the beams 611 and 612 include, respectively, a plurality of beamlets C1, . . . , C9 and D1, . . . , D9, each of which shows an intensity variation along the horizontal dimension corresponding to that of the beamlets B1, . . . , B9. Further, the beams C1, . . . , C9 and D1, . . . , D9 have optical frequencies $f_1, \ldots, f_9$, corresponding to the optical frequencies of the beamlets B1, . . . , B9.

Figure 14D:
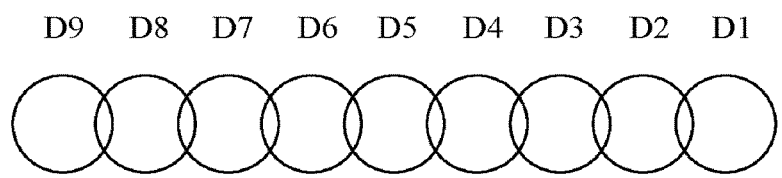
FIG. 14D shows a horizontally inverted version of the beam depicted in FIG. 14C.
Figure 15:
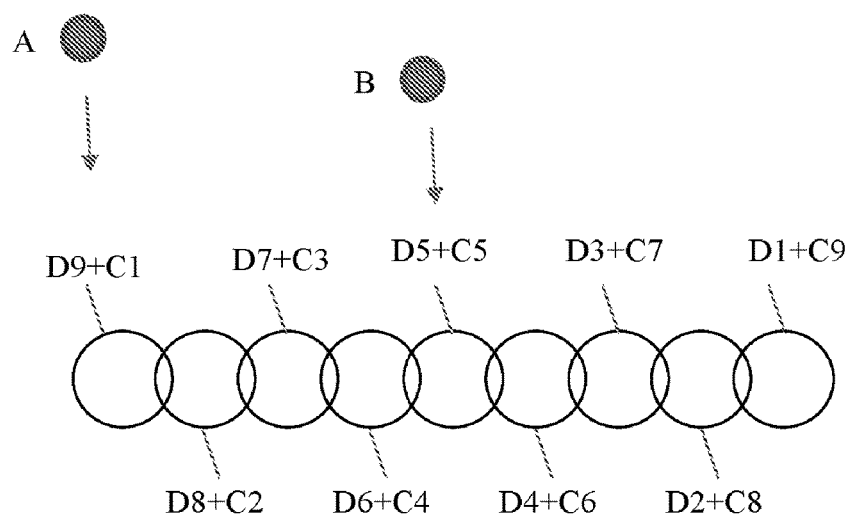
FIG. 15 schematically exhibits an excitation beam formed by superposition of two sets of beamlets.

The beam 612 is reflected by a mirror 614 and is received by a dove prism 616. The passage of the beam 612 through the dove prism 616 results in a horizontal inversion of the beam. In other words, the dove prism 616 horizontally inverts the beam 612 to generate a horizontally inverted beam 618 in which the ordering of the beamlets D1, . . . , D9 is spatially inverted, as shown in FIG. 14D, such that the beamlet D9 forms the left horizontal edge of the inverted beam 618 and the beamlet D1 forms the right edge of the inverted beam. The inverted beam 618 propagates to an optical beam combiner 620, which combines the inverted beam 618 with the beam 611, as discussed below.

In particular, the beam 611 propagates to a mirror 622, which reflects the beam 611 to the optical beam combiner 620. The beam 611 is reflected by the optical beam combiner 620 to be superimposed on the inverted beam 611 that passes through the beam combiner 620 to form a combined excitation beam 624. The beam combiner is configured such that the beams 611 and 618 are superimposed on one another such that the beamlets forming the two beams are substantially aligned pairwise in the combined excitation beam 624. More specifically, in the combined excitation beam 624, the beamlet D9, D8, D7, D6, D5, D4, D3, D2 and D1 are superimposed, respectively, on beamlets C1, C2, C3, C4, C5, C6, C7, C8, and C9.

A convergent lens 626 focused the combined excitation beam into a flow cell 628 so as to excite a plurality of particles (e.g., cells) flowing through the cell. The radiation emanating from the particles in response to the excitation beam (e.g., scattered and/or fluorescence radiation) can be collected and analyzed, as discussed in more detail below.

As a particle passes through a portion of the excitation beam formed by superposition of two beamlets, it is exposed to a superposition of their electric fields. Thus, the radiation emitted by the particle exhibits a beat frequency corresponding to a difference between the optical frequencies of those beamlets. By way of example and with reference to FIG. 15, the radiation emitted by a particle A passing through the left horizontal edge of the excitation beam, which is formed via a superposition of the beamlets D9 and C1, would exhibit a beat frequency corresponding to the difference between the frequencies of the beamlets D9 and C1, i.e., a beat frequency of $f_9-f_1$. The radiation emitted by another particle B passing through the center of the excitation beam formed by a superposition of the beamlets D5 and C5 would exhibit a vanishing beat frequency as the frequencies of D5 and C5 are identical. In this manner, the positions of the particles passing through the excitation beam can be encoded via the RF beat frequencies associated with the radiation emitted by those particles. As discussed in more detail below, in some embodiments, such encoding of the positions of the particles can be used to normalize the intensity of the detected radiation emitted by those particles relative to the variation of the beam intensity, e.g., across its horizontal direction.

Similar to the previous embodiment, in this embodiment, the intensity of the excitation beam varies across its horizontal dimension with a maximum intensity at its horizontal edges and a minimum intensity at its center. This variation of the intensity can compensate, for example, the lower detection efficiency for radiation emitted from those particles that pass through the horizontal edges of the excitation beam.

Referring again to FIG. 13, the radiation scattered from the particles in the forward direction, in response to their interaction with the excitation beam, is focused by a lens 630 onto a photodetector 632. A bandpass filter 634 disposed in front of the photodetector 632 allows transmission of the excitation wavelength while blocking undesired wavelengths.

The radiation emitted from the particles (e.g., scattered and/or fluorescence radiation) in a direction orthogonal to the forward direction by an objective lens 636 and is focused by a convergent lens 638 onto a proximal end (PE) of a multi-mode optical fiber 640. An outcoupling lens 642 collimates the radiation exiting the optical fiber 640 and a plurality of dichroic mirrors 644, 646, and 648 distribute the collimated radiation onto a plurality of photomultiplier tubes 650, 652, 654, and 656 in a manner discussed above in connection with the previous embodiment. Further, similar to the previous embodiment, a plurality of bandpass filters 650*a*, 652*a*, 654*a* and 656*a* are disposed in front of the photomultiplier tubes 650, 652, 654, and 656, respectively. The bandpass filters can be selected to allow passage of specific radiation wavelengths onto the photomultipliers while blocking other wavelengths.

An analyzer 660 receives the signals generated by the photodetector 632 and the photomultipliers 650, 652, 654, and 656. The analyzer can decode the RF encoding of these signals by determining the frequency content of the detected signals. A variety of methods for determining the frequency content of the detected signals can be used. Some examples of such suitable methods include, without limitation, Fourier transform, lock-in detection, filtering, I/Q demodulation, homodyne detection, and heterodyne detection.

By way of example, a detected signal (e.g., a signal detected by the photodetector or one of the photomultipliers) can be digitized and an appropriate portion of the digitized signal can be selected for analysis. A Fast Fourier Transform (FFT) of the selected data can be performed to determine the frequency components of the detected signal. In some such embodiments, the bins of the FFT can correspond to the frequencies chosen for data acquisition. For example, for a 256 MHz sampling rate, 256 samples can yield frequency bins that are separated from one another by 1 MHz, e.g., from DC to 128 MHz. The FFT analysis provides frequencies corresponding to the beat frequencies present in the detected signal. A measure of the amplitude of each frequency component present in the FFT data can be computed, for example, by obtaining the square root of the sum of squares of the real and imaginary components of that frequency component.

Each beat frequency extracted from the detected signal can be associated with radiation emitted from particles passing through a portion of the beam formed by superposition of two beamlets having a frequency difference equal to that beat frequency. As such, each frequency component of the detected signal can be correlated to a particular position along the excitation beam. When the particles passing through the flow cell are identical, variations in the amplitudes of the beat frequencies can be indicative of variation in the intensity along the excitation beam and/or differences in the efficiency of radiation detection system with respect to radiation emitted by particles flowing through different portions of the beam. As such, the amplitudes of the beat frequencies can be utilized to computationally compensate for such variations so as to compute a normalized detection signal. Using knowledge of the position of the particle encoded by the detected beat frequency in combination with knowledge of the optical intensity of the excitation beam at that position, the intensity of the detected signal can be normalized by dividing the detected signal by a scale factor, e.g., in a look up table of normalization data. This look up table can be calibrated by measuring signal intensities from flowing homogeneous reference particles as they flow by the beam in multiple horizontal locations. Alternatively, a narrow core stream (e.g., less than 5 microns in width) can be mechanically scanned across the beam by moving the flow cell relative to the excitation beam, such that the lateral position of particles crossing the excitation beam is known, and the signal intensities can be measured for calibration purposes.

The controller and the analyzer in this embodiment can be implemented, for example, in a manner discussed above in connection with the controller and the analyzer in the previous embodiment.

Computer-Controlled Systems

Aspects of the present disclosure further include computer controlled systems for practicing the subject methods, where the systems further include one or more computers for complete automation or partial automation of a system for practicing methods described herein. In some embodiments, systems include a computer having a computer readable storage medium with a computer program stored thereon, where the computer program when loaded on the computer includes instructions for irradiating with a laser while applying radiofrequency drive signals to the acousto-optic device to generate angularly deflected laser beams and adjusting the amplitude of one or more of the radiofrequency drive signals to generate an output laser beam that comprises angularly deflected laser beams with a predetermined intensity profile. Each angularly deflected laser beam in the output laser beam has an intensity that is based on the amplitude of each applied radiofrequency drive signal.

In embodiments, the system includes an input module, a processing module and an output module. In some embodiments, the subject systems may include an input module such that parameters or information about the acousto-optic device (e.g., acousto-optic deflector), the laser, the source of radiofrequency drive signals (e.g., a direct digital synthesizer), the sample, intensity and wavelengths (discrete or ranges) of the applied light source, flow cell diameter, number of light channels, number of detection regions, duration of irradiation by the light source, number of different light sources, distance from light source to the flow channel, focal length of any optical adjustment components, refractive index of flow channel medium (e.g., sheath fluid), presence of any wavelength separators, properties of wavelength separators including bandpass width, opacity, grating spacing as well as properties and sensitivity of the photodetectors.

After the processing module has performed one or more of the steps of the subject methods, an output module communicates the results to the user, such as by displaying on a monitor or by printing a report.

The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system.

Systems may include a display and operator input device. Operator input devices may, for example, be a keyboard, mouse, or the like. The processing module includes a processor which has access to a memory having instructions stored thereon for performing the steps of the subject methods, such as irradiating with a laser while applying radiofrequency drive signals to the acousto-optic device to generate angularly deflected laser beams and adjusting the amplitude of one or more of the radiofrequency drive signals to generate an output laser beam that comprises angularly deflected laser beams with a predetermined intensity profile.

The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Memory may be any suitable device in which the processor can store and retrieve data, such as magnetic, optical, or solid state storage devices (including magnetic or optical disks or tape or RAM, or any other suitable device, either fixed or portable). The processor may include a general purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; portable flash drive; and hybrids of these categories such as magnetic/optical storage media.

The processor may also have access to a communication channel to communicate with a user at a remote location. By remote location is meant the user is not directly in contact with the system and relays input information to an input manager from an external device, such as a computer connected to a Wide Area Network ("WAN"), telephone network, satellite network, or any other suitable communication channel, including a mobile telephone (i.e., smartphone).

In some embodiments, systems according to the present disclosure may be configured to include a communication interface. In some embodiments, the communication interface includes a receiver and/or transmitter for communicating with a network and/or another device. The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

In one embodiment, the communication interface is configured to include one or more communication ports, e.g., physical ports or interfaces such as a USB port, an RS-232 port, or any other suitable electrical connection port to allow data communication between the subject systems and other external devices such as a computer terminal (for example, at a physician's office or in hospital environment) that is configured for similar complementary data communication.

In one embodiment, the communication interface is configured for infrared communication, Bluetooth® communication, or any other suitable wireless communication protocol to enable the subject systems to communicate with other devices such as computer terminals and/or networks, communication enabled mobile telephones, personal digital assistants, or any other communication devices which the user may use in conjunction therewith, in managing the treatment of a health condition, such as HIV, AIDS or anemia.

In one embodiment, the communication interface is configured to provide a connection for data transfer utilizing Internet Protocol (IP) through a cell phone network, Short Message Service (SMS), wireless connection to a personal computer (PC) on a Local Area Network (LAN) which is connected to the internet, or WiFi connection to the internet at a WiFi hotspot.

In one embodiment, the subject systems are configured to wirelessly communicate with a server device via the communication interface, e.g., using a common standard such as 802.11 or Bluetooth® RF protocol, or an IrDA infrared protocol. The server device may be another portable device, such as a smart phone, Personal Digital Assistant (PDA) or notebook computer; or a larger device such as a desktop computer, appliance, etc. In some embodiments, the server device has a display, such as a liquid crystal display (LCD), as well as an input device, such as buttons, a keyboard, mouse or touch-screen.

In some embodiments, the communication interface is configured to automatically or semi-automatically communicate data stored in the subject systems, e.g., in an optional data storage unit, with a network or server device using one or more of the communication protocols and/or mechanisms described above.

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module to a user at a remote location, e.g., over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT®, Windows XP, Windows 7, Windows 8, iOS, Sun Solaris, Linux, OS/400, Compaq Tru64 Unix, SGI IRIX, Siemens Reliant Unix, and others.

Kits

Aspects of the invention further include kits, where kits include one or more of a flow cell configured to propagate a sample in a flow stream, an acousto-optic device and an optical adjustment component (e.g., beam splitter, beam inverter such as a dove prism) as described herein. In some embodiments, kits further include a laser. In certain instances, kits can include one or more assay components (e.g., labeled reagents, buffers, etc., such as described above). In some instances, the kits may further include a sample collection device, e.g., a lance or needle configured to prick skin to obtain a whole blood sample, a pipette, etc., as desired. The subject kits may also include a waste collection container.

In some embodiments, kits include a fluidic composition, such as a digestive enzyme composition or buffer solution. Example buffers may include but are not limited to PBS (phosphate) buffer, acetate buffer, N,N-bis(2-hydroxyethyl) glycine (Bicine) buffer, 3-{[tris(hydroxymethyl)methyl]amino}propanesulfonic acid (TAPS) buffer, 2-(N-morpholino)ethanesulfonic acid (MES) buffer, citrate buffer, tris(hydroxymethyl)methylamine (Tris) buffer, N-tris(hydroxymethyl)methylglycine (Tricine) buffer, 3-[N-Tris(hydroxymethyl)methylamino]-2-hydroxypropanesulfonic Acid (TAPSO) buffer, 4-2-hydroxyethyl-1-piperazineethanesulfonic acid (HEPES) buffer, 2-{[tris(hydroxymethyl)methyl]amino}ethanesulfonic acid (TES) buffer, piperazine-N,N'-bis(2-ethanesulfonic acid) (PIPES) buffer, dimethylarsinic acid (Cacodylate) buffer, saline sodium citrate (SSC) buffer, 2(R)-2-(methylamino)succinic acid (succinic acid) buffer, potassium phosphate buffer, N-Cyclohexyl-2-aminoethanesulfonic acid (CHES) buffer, among other types of buffered solutions. In certain instances, the fluidic composition is a cytometer-grade solution.

In still other embodiments, kits include a labelling reagent composition. For example, the labelling reagent composition may be a fluorophore, chromophore, enzyme, redox label, radiolabels, acoustic label, Raman (SERS) tag, mass tag, isotope tag, magnetic particle, microparticle or nanoparticle or a combination thereof. In some cases, the labelling reagent includes a labelled biomolecule, such as a polypeptide, a nucleic acid and a polysaccharide that is labelled with a fluorophore, chromophore, enzyme, redox label, radiolabels, acoustic label, Raman (SERS) tag, mass tag, isotope tag, magnetic particle, microparticle or nanoparticle or a combination thereof.

The various assay components of the kits may be present in separate containers, or some or all of them may be pre-combined. For example, in some instances, one or more components of the kit, e.g., each detector is present in a sealed pouch, e.g., a sterile foil pouch or envelope.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), portable flash drive, and the like, on which the information has been recorded. Yet another form of these instructions that may be present is a website address which may be used via the internet to access the information at a removed site.

Utility

The subject methods, systems and computer systems for producing an output laser beam having two or more angularly deflected laser beams (e.g., for irradiating a sample in a flow stream) with a predetermined intensity profile find use in a variety of applications where it is desirable to analyze and sort particle components in a sample in a fluid medium, such as a biological sample. Embodiments of the invention find use where it is desirable to provide an improved analysis of sample composition, cell sorting accuracy and enhanced sub-particle detection.

Embodiments of the invention also find use in applications where cells prepared from a biological sample may be desired for research, laboratory testing or for use in therapy. In some embodiments, the subject methods and devices may facilitate obtaining individual cells prepared from a target fluidic or tissue biological sample. For example, the subject methods and systems facilitate obtaining cells from fluidic or tissue samples to be used as a research or diagnostic specimen for diseases such as cancer. Likewise, the subject methods and systems may facilitate obtaining cells from fluidic or tissue samples to be used in therapy. Methods and devices of the present disclosure allow for detecting and collecting cells from a biological sample (e.g., organ, tissue, tissue fragment, fluid) with enhanced efficiency and low cost as compared to traditional flow cytometry systems.

Notwithstanding the appended clauses, the disclosure set forth herein is also defined by the following clauses:

1. A method for generating an excitation beam for use in a flow cytometry system, comprising:
    introducing a laser beam into an acousto-optic device,
    applying a plurality of radiofrequency signals to said acousto-optic device so as to generate a plurality of partially overlapping angularly deflected beams collectively forming an output excitation beam, and
    adjusting amplitudes of said radiofrequency signals such that said output excitation beam exhibits a desired intensity profile.

2. The method of clause 1, wherein said acousto-optic device is an acousto-optic deflector.

3. The method of clause 1, wherein said intensity profile is characterized by an intensity variation along a horizontal dimension of the beam.

4. The method of clause 3, wherein said beam intensity variation is characterized by an intensity increase from a center of the beam to each horizontal edge thereof.

5. The method of clause 4, wherein the beam intensity at the center of the beam varies by a value in a range about 0.1% to about 99% relative to the intensity of the beam at each of said horizontal edges.

6. The method of clause 3, wherein said intensity profile exhibits a Gaussian intensity distribution along a vertical dimension of the beam.

7. The method of clause 3, wherein the amplitudes of said radiofrequency signals are in a range of about 0.1 volts to about 40 volts.

8. The method of clause 1, wherein said radiofrequency signals span a frequency range of about 1 MHz to about 250 MHz.

9. The method of clause 8, wherein said radiofrequency signals are separated from one another by a frequency in a range of about 0.1 MHz to about 4 MHz.

10. The method of clause 1, wherein the amplitudes of said radiofrequency signals are adjusted such that the deflected beams exhibit an increasing intensity as the deflection angles of the beams increases away from a center beam.

11. A flow cytometry system, comprising:
    a flow cell through which a plurality of particles can flow,
    a laser for generating a laser beam,
    an acousto-optic device receiving said laser beam,
    at least one radiofrequency generator for applying a plurality of radiofrequency signals to said acousto-optic device so as to generate a plurality of partially overlapping angularly deflected beams collectively forming an output excitation beam for illuminating a plurality of particles flowing through said flow cell,
    a controller coupled to said at least one radiofrequency generator for adjusting powers of said radiofrequency signals so as to impart a intensity profile to said excitation beam characterized by variation of the intensity along at least one dimension of the beam.

12. The flow cytometry system of clause 11, further comprising a detection system for detecting radiation emanating from said illuminated particles in response to the illumination by said excitation beam.

13. The flow cytometry system of clause 12, wherein said intensity profile is configured such that equivalent particles interacting with the beam at different locations thereof produce uniform signals.

14. The flow cytometry system of clause 11, wherein said intensity profile is characterized by an intensity variation along a horizontal dimension of said beam.

15. The flow cytometry system of clause 14, wherein said beam intensity variation is characterized by an intensity increase from a center of the beam to each horizontal edge thereof.

16. The flow cytometry system of clause 14, wherein the beam intensity at the center of the beam varies by at least about 50% relative to the intensity of the beam at each of said horizontal edges.

17. The flow cytometry system of clause 14, wherein said intensity profile exhibits a Gaussian intensity distribution along a vertical dimension of the beam.

18. The flow cytometry system of clause 11, wherein said controller adjusts the powers of said radiofrequency signals such that the deflected beams exhibit an increasing intensity as the deflection angles of the beams increase away from a center beam.

19. The flow cytometry system of clause 11, wherein said controller adjusts the powers of the radiofrequency signals by adjusting amplitudes thereof in a range of about 0.1 volts to about 40 volts.

20. The flow cytometry system of clause 11, wherein said controller controls said radiofrequency generator so as to generate a plurality of radiofrequency signals separated from one another by a frequency in range of about 0.1 MHz to about 4 MHz.

21. The flow cytometry system of clause 11, further comprising one or more excitation optics for delivering said excitation beam to said flow cell.

22. The flow cytometry system of clause 21, wherein said one or more excitation optics comprises at least one lens for focusing said excitation beam onto said illuminated cells.

23. The flow cytometry system of clause 21, wherein detection system comprises at least one detector and one or more detection optics positioned at 90 degrees relative to propagation direction of the excitation beam for transmitting the radiation emanating from the illuminated cells in response to the illumination to said detector.

24. The flow cytometry system of clause 11, wherein said particles comprise a plurality of cells.

25. A method for adjusting an intensity profile of an excitation beam in a flow cytometry system, comprising:
introducing a laser beam into an acousto-optic device,
applying a plurality of radiofrequency signals to said acousto-optic device to generate a plurality of angularly separated output beams,
adjusting amplitudes of said radiofrequency signals to obtain a desired intensities of said angularly separated output beams.

26. The method of clause 25, wherein said acousto-optic device is an acousto-optic deflector.

27. The method of clause 25, wherein the step of adjusting the amplitudes comprises varying the rms amplitudes of said radiofrequency signals in a range of about 0.1 volts to about 40 volts.

28. The method of clause 25, wherein said radiofrequency signals are separated in frequency by a value in a range of about 0.1 MHz to about 4 MHz.

29. The method of clause 25, wherein said angularly separated output beams are arranged relative to one another so as to form collectively an excitation beam for illuminating a plurality of particles flowing through a flow cell of said flow cytometry system.

30. The method of clause 29, wherein said amplitudes are adjusted such that said excitation beam exhibits a higher intensity at each edge thereof relative to its center.

31. The method of clause 30, wherein said intensity variation between each edge and the center of the beam is at least about 50%.

32. A flow cytometry system, comprising:
a flow cell through which a plurality of particles can flow,
a laser for generating a laser beam,
an acousto-optic device receiving said laser beam,
at least one radiofrequency generator for applying a plurality of radiofrequency signals to said acousto-optic device so as to generate a plurality angularly-deflected beamlets separated in frequency by said radiofrequency signals and collectively forming a radiofrequency-shifted laser beam,
a beam splitter for splitting said radiofrequency-shifted laser beam into a pair of split radiofrequency-shifted laser beams such that each of the split beams includes a plurality of angularly-deflected beamlets separated in frequency by said radiofrequency signals,
at least one optic for horizontally inverting one of said pair of laser beams, an optical combiner for combining said horizontally inverted beam with the other beam of the pair such that each of the beamlets in the horizontally inverted beam at least partially overlaps with at least one of the beamlets in the other beam of the pair so as to generate an excitation beam for illuminating said particles as they flow through the flow cell.

33. The flow cytometry system of clause 32, further comprising at least one detector for detecting forward scatter radiation emanating from one or more of said particles in response to excitation from said excitation beam and generating a detection signal.

34. The flow cytometry system of clause 33, further comprising an analyzer for receiving said detection signal and providing frequency de-multiplexing of the detection signal so as to determine one or more beat frequencies, wherein each of the beat frequencies corresponds to a frequency difference between a pair of at least partially overlapping beamlets in said excitation beam.

35. The flow cytometry system of clause 34, wherein said analyzer further correlates said one or more beat frequencies with spatial locations across the excitation beam.

36. The flow cytometry system of clause 35, wherein said analyzer normalizes the intensity the detected forward scatter signal based on the spatial location in the excitation beam associated with the beat frequency present in frequency content of the forward scatter signal.

37. The flow cytometry system of clause 32, further comprising a controller coupled to said at least one radiofrequency generator for adjusting amplitudes of said radiofrequency signals so as to adjust intensities of said beamlets such that intensity of said radiofrequency-modulated beam varies along a horizontal dimension.

38. The flow cytometry system of clause 37, wherein said radiofrequency signals are shifted in frequency relative to one another by a frequency in a range of about 10 MHz to about 250 MHz.

39. A method of adjusting spatial position of an excitation beam in a flow cytometer, comprising:
introducing a laser beam into an acousto-optic deflector,
applying a plurality of radiofrequency signals to said acousto-optic deflector so as to generate a plurality of partially overlapping angularly deflected beams collectively forming an output excitation beam,
introducing the excitation beam into a flow cell to interact with a sample stream flowing through the flow cell,
monitoring a signal generated via detection of radiation emanating from the sample in response to interaction with the excitation beam to detect a spatial drift, if any, in the sample stream,
adjusting said radiofrequency signals so as to adjust a spatial position of the excitation beam in the flow cell so as to compensate for the detected drift in the sample stream.

40. The method of clause 39, wherein the step of adjusting the radiofrequency signals comprises adjusting frequencies of said radiofrequency signals.

41. A method of adjusting a width of an excitation beam in a flow cytometer, comprising:
introducing a laser beam into an acousto-optic deflector,
applying a plurality of radiofrequency signals to said acousto-optic deflector so as to generate a plurality of partially overlapping angularly deflected beams collectively forming an output excitation beam, and
adjusting a number of said radiofrequency signals so as to adjust a width of said excitation beam.

42. A method comprising:
irradiating an acousto-optic device with a laser; and
applying a first radiofrequency drive signal and a second radiofrequency drive signal to the acousto-optic device to generate a first angularly deflected laser beam and a second angularly deflected laser beam,
wherein the first angularly deflected laser beam has an intensity that is based on the amplitude of the first applied radiofrequency drive signal and the second angularly deflected laser beam has an intensity that is based on the amplitude of the second applied radiofrequency drive signal; and adjusting the amplitude of one or more of the first radiofrequency drive signal and the second radiofrequency drive signal to generate an output laser beam that comprises the first angularly deflected laser beam having a first intensity and the second angularly deflected laser beam having a second intensity.

43. The method of clause 42, wherein the method comprises applying a plurality of radiofrequency drive signals to the acousto-optic device to generate a plurality of angularly deflected laser beams, wherein each angularly deflected laser beam has an intensity that is based on each applied radiofrequency drive signal.

44. The method of any one of clauses 42-43, wherein the acousto-optic device is an acousto-optic deflector.

45. The method of any one of clauses 42-44, wherein the angularly deflected laser beams are spatially separated.

46. The method of clause 45, wherein the angularly deflected laser beams at least partially overlap.

47. The method of any one of clauses 45-46, wherein the angularly deflected laser beams are aligned along a horizontal axis in the output laser beam.

48. The method of any one of clauses 42-47, wherein two or more of the angularly deflected laser beams in the output laser beam have the same intensity.

49. The method of any one of clauses 42-47, wherein two or more of the angularly deflected laser beams in the output laser beam have different intensities.

50. The method of any one of clauses 42-47, wherein the angularly deflected laser beams in the output laser beam have a predetermined intensity profile along a horizontal axis.

51. The method of clause 50, wherein the intensity profile comprises increasing intensity from the center to the edges of the output laser beam along the horizontal axis.

52. The method of clause 51, wherein the intensity of the angularly deflected laser beam at the center of the output beam is from 0.1% to about 99% of the intensity of the angularly deflected laser beams at the edge of the output laser beam along the horizontal axis.

53. The method of clause 50, wherein the intensity profile comprises an increasing intensity from the edges to the center of the output laser beam along the horizontal axis.

54. The method of clause 50, wherein the intensity profile comprises a Gaussian distribution along the horizontal axis of the output laser beam.

55. The method of clause 50, wherein the output laser beam has a top hat intensity profile along the horizontal axis.

56. The method of clause 50, wherein each angularly deflected laser beam of the output laser beam has substantially the same intensity.

57. The method of clause 50, wherein the intensity profile comprises an increasing intensity from a first edge of the output laser beam to a second edge of the output laser beam along the horizontal axis.

58. The method of any one of clauses 50-57, wherein the intensity profile comprises a Gaussian distribution along a vertical axis of the output laser beam.

59. The method of any one of clauses 42-58, wherein each radiofrequency drive signal is independently from about 1 MHz to about 250 MHz.

60. The method of any one of clauses 42-58, wherein each radiofrequency drive signal has an amplitude that is independently from about 0.1 volts to about 40 volts.

61. The method of any one of clauses 42-60, further comprising adjusting the spatial width of the output laser beam.

62. The method of clause 61, wherein adjusting the spatial width of the output laser beam comprises reducing the spatial width of the output laser beam by reducing the number of applied radiofrequency drive signals.

63. The method of clause 62, wherein adjusting the spatial width of the output laser beam comprises increasing the spatial width of the output laser beam by increasing the number of applied radiofrequency drive signals.

64. The method of any one of clauses 61-63, further comprising:
irradiating a sample in a flow stream with the output laser beam; and
detecting light from the sample in the flow stream.

65. The method of clause 64, further comprising measuring the detected light at one or more wavelengths.

66. The method of any one of clauses 64-65, wherein the detected light is forward scattered light, side scattered light, transmitted light, emitted light or a combination thereof.

67. The method of any one of clauses 64-66, further comprising monitoring the detected light from the sample in the flow stream to detect spatial drift of the output laser beam.

68. The method of clause 67, further comprising adjusting the spatial position of the output laser beam on the flow stream when spatial drift is detected.

69. The method of clause 68, wherein adjusting the spatial position comprises adjusting the frequency of the applied radiofrequency drive signals.

70. The method of any one of clauses 42-69, further comprising producing a first split laser beam comprising a first set of angularly deflected laser beams and a second split laser beam comprising a second set of angularly deflected laser beams from the output laser beam.

71. The method of clause 70, wherein the first split laser beam and the second split laser beam comprise an identical set of angularly deflected laser beams.

72. The method of clause 71, wherein the angularly deflected laser beams are identical in one or more of the quantity, amplitude and frequency.

73. The method of any of clauses 70-72, further comprising:
inverting the first split laser beam; and
optically combining the inverted first split laser beam with the second split laser beam to produce a combined output laser beam,
wherein the first set of angularly deflected laser beams are inverted and overlap with the second set of angularly deflected laser beams.

74. The method of any one of clauses 70-73, further comprising:
irradiating a sample in a flow stream with the combined output laser beam; and
detecting light from the sample in the flow stream.

75. The method of clause 74, further comprising measuring the detected light at one or more wavelengths.

76. The method of any one of clauses 74-75, wherein the detected light is forward scattered light, side scattered light, transmitted light, emitted light or a combination thereof.

77. A system comprising:
a laser;
an acousto-optic device;
a radiofrequency generator configured to apply a first radiofrequency drive signal and a second radiofrequency drive signal to the acousto-optic device to generate a first angularly deflected laser beam and a second angularly deflected laser beam, wherein the first angularly deflected laser beam has an intensity that is based on the amplitude of the first applied radiofrequency drive signal and the second angularly deflected laser beam has an intensity that is based on the amplitude of the second applied radiofrequency drive signal; and a controller comprising a processor having memory operably coupled to the processor wherein the memory comprises instructions stored thereon, which when executed by the processor, cause the processor to adjust the amplitude of one or more of the first radiofrequency drive signal and the second radiofrequency drive signal to generate an output laser beam that comprises the first angularly deflected laser beam having a first intensity and the second angularly deflected laser beam having a second intensity.

78. The system of clause 77, wherein the radiofrequency generator is configured to apply a plurality of radiofrequency drive signals to the acousto-optic device to generate a plurality of angularly deflected laser beams, wherein each angularly deflected laser beam has an intensity that is based on each applied radiofrequency drive signal.

79. The system of any one of clauses 77-78, wherein the acousto-optic device is an acousto-optic deflector.

80. The system of any one of clauses 77-79, wherein the angularly deflected laser beams are spatially separated.

81. The system of clause 80, wherein the angularly deflected laser beams at least partially overlap.

82. The system of any one of clauses 77-81, wherein the angularly deflected laser beams are aligned along a horizontal axis in the output laser beam.

83. The system of any one of clauses 77-81, wherein two or more of the angularly deflected laser beams in the output laser beam have the same intensity.

84. The system of any one of clauses 77-81, wherein two or more of the angularly deflected laser beams in the output laser beam have different intensities.

85. The system of any one of clauses 77-81, wherein the angularly deflected laser beams in the output laser beam have a predetermined intensity profile along a horizontal axis.

86. The system of clause 85, wherein the intensity profile comprises increasing intensity from the center to the edges of the output laser beam along the horizontal axis.

87. The system of clause 86, wherein the intensity of the angularly deflected laser beam at the center of the output beam is from 0.1% to about 99% of the intensity of the angularly deflected laser beams at the edge of the output laser beam along the horizontal axis.

88. The system of clause 85, wherein the intensity profile comprises an increasing intensity from the edges to the center of the output laser beam along the horizontal axis.

89. The system of clause 85, wherein the intensity profile comprises a Gaussian distribution along the horizontal axis of the output laser beam.

90. The system of clause 85, wherein the output laser beam has a top hat intensity profile along the horizontal axis.

91. The system of clause 85, wherein each angularly deflected laser beam of the output laser beam has substantially the same intensity.

92. The system of clause 85, wherein the intensity profile comprises an increasing intensity from a first edge of the output laser beam to a second edge of the output laser beam along the horizontal axis.

93. The system of any one of clauses 85-92, wherein the intensity profile comprises a Gaussian distribution along a vertical axis of the output laser beam.

94. The system of any one of clauses 77-93, wherein each radiofrequency drive signal is independently from about 1 MHz to about 250 MHz.

95. The system of any one of clauses 77-94, wherein each radiofrequency drive signal has an amplitude that is independently from about 0.1 volts to about 40 volts.

96. The system of any one of clauses 77-95, wherein the memory comprises instructions stored thereon, which when executed by the processor, cause the processor to adjust the spatial width of the output laser beam.

97. The system of clause 96, wherein adjusting the spatial width of the output laser beam comprises reducing the spatial width of the output laser beam by reducing the number of applied radiofrequency drive signals.

98. The system of clause 96, wherein adjusting the spatial width of the output laser beam comprises increasing the spatial width of the output laser beam by increasing the number of applied radiofrequency drive signals.

99. The system of any one of clauses 77-98, further comprising:
a flow cell configured to propagate a sample in a flow stream; and
a detector for detecting light from the sample in the flow stream.

100. The system of clause 99, wherein the detector is configured to measure the detected light at one or more wavelengths.

101. The system of any one of clauses 99-100, wherein the detected light is forward scattered light, side scattered light, transmitted light, emitted light or a combination thereof.

102. The system of any one of clauses 99-101, wherein the memory comprises instructions stored thereon, which when executed by the processor, cause the processor to monitor the detected light from the sample in the flow stream to detect spatial drift of the output laser beam.

103. The system of clause 102, wherein the memory comprises instructions stored thereon, which when executed by the processor, cause the processor to adjust the spatial position of the output laser beam on the flow stream when spatial drift is detected.

104. The system of clause 103, wherein the memory comprises instructions stored thereon, which when executed by the processor, cause the processor to adjust the frequency of the applied radiofrequency drive signals.

105. The system of any one of clauses 77-104, further comprising a beam splitter for producing a first split laser beam comprising a first set of angularly deflected laser beams and a second split laser beam comprising a second set of angularly deflected laser beams from the output laser beam.

106. The system of clause 105, wherein the first split laser beam and the second split laser beam comprise an identical set of angularly deflected laser beams.

107. The system of clause 106, wherein the angularly deflected laser beams are identical in one or more of the quantity, amplitude and frequency.

108. The system of any of clauses 105-107, further comprising:
a first optical adjustment component for inverting the first split laser beam; and
a second optical adjustment component for optically combining the inverted first split laser beam with the second split laser beam to produce a combined output laser beam,
wherein the first set of angularly deflected laser beams are inverted and overlap with the second set of angularly deflected laser beams.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method comprising:
   irradiating an acousto-optic device with a laser; and
   applying a first radiofrequency drive signal and a second radiofrequency drive signal to the acousto-optic device to generate a first angularly deflected laser beam and a second angularly deflected laser beam,
      wherein the first angularly deflected laser beam has an intensity that is based on the amplitude of the first applied radiofrequency drive signal and the second angularly deflected laser beam has an intensity that is based on the amplitude of the second applied radiofrequency drive signal; and
   adjusting the amplitude of one or more of the first radiofrequency drive signal and the second radiofrequency drive signal to generate an output laser beam that comprises the first angularly deflected laser beam having a first intensity and the second angularly deflected laser beam having a second intensity.

2. The method of claim 1, wherein the method comprises applying a plurality of radiofrequency drive signals to the acousto-optic device to generate a plurality of angularly deflected laser beams, wherein each angularly deflected laser beam has an intensity that is based on each applied radiofrequency drive signal.

3. The method of claim 1, wherein the acousto-optic device is an acousto-optic deflector.

4. The method of claim 1, wherein the angularly deflected laser beams are spatially separated.

5. The method of claim 4, wherein the angularly deflected laser beams at least partially overlap.

6. The method of claim 4, wherein the angularly deflected laser beams are aligned along a horizontal axis in the output laser beam.

7. The method of claim 1, wherein the angularly deflected laser beams in the output laser beam have a predetermined intensity profile along a horizontal axis.

8. The method of claim 7, wherein the intensity profile comprises increasing intensity from the center to the edges of the output laser beam along the horizontal axis.

9. The method of claim 8, wherein the intensity of the angularly deflected laser beam at the center of the output beam is from 0.1% to about 99% of the intensity of the angularly deflected laser beams at the edge of the output laser beam along the horizontal axis.

10. The method of claim 7, wherein the intensity profile comprises an increasing intensity from the edges to the center of the output laser beam along the horizontal axis.

11. The method of claim 7, wherein the intensity profile comprises a Gaussian distribution along a vertical axis of the output laser beam.

12. The method of claim 1, wherein each radiofrequency drive signal is independently from about 1 MHz to about 250 MHz.

13. The method of claim 1, wherein each radiofrequency drive signal has an amplitude that is independently from about 0.1 volts to about 40 volts.

14. The method of claim 1, further comprising adjusting the spatial width of the output laser beam by reducing or increasing the number of applied radiofrequency drive signals.

15. The method of claim 1, further comprising:
   irradiating a sample in a flow stream with the output laser beam; and
   detecting light from the sample in the flow stream.

16. The method of claim 15, further comprising:
   monitoring the detected light from the sample in the flow stream to detect spatial drift of the output laser beam; and
   adjusting the frequency of the applied radiofrequency drive signals when spatial drift is detected.

17. The method of claim 1, further comprising producing a first split laser beam comprising a first set of angularly deflected laser beams and a second split laser beam comprising a second set of angularly deflected laser beams from the output laser beam.

18. The method of claim 17, wherein the first split laser beam and the second split laser beam comprise an identical set of angularly deflected laser beams in one or more of the quantity, amplitude and frequency.

19. The method of claim 17, further comprising:
   inverting the first split laser beam; and
   optically combining the inverted first split laser beam with the second split laser beam to produce a combined output laser beam,
   wherein the first set of angularly deflected laser beams are inverted and overlap with the second set of angularly deflected laser beams.

20. A system comprising:
   a laser;
   an acousto-optic device;
   a radiofrequency generator configured to apply a first radiofrequency drive signal and a second radiofrequency drive signal to the acousto-optic device to generate a first angularly deflected laser beam and a second angularly deflected laser beam,
      wherein the first angularly deflected laser beam has an intensity that is based on the amplitude of the first applied radiofrequency drive signal and the second angularly deflected laser beam has an intensity that is based on the amplitude of the second applied radiofrequency drive signal; and
   a controller comprising a processor having memory operably coupled to the processor wherein the memory comprises instructions stored thereon, which when executed by the processor, cause the processor to adjust the amplitude of one or more of the first radiofrequency drive signal and the second radiofrequency drive signal to generate an output laser beam that comprises the first angularly deflected laser beam having a first intensity and the second angularly deflected laser beam having a second intensity.

* * * * *